US012790321B2

(12) United States Patent
Song et al.

(10) Patent No.: US 12,790,321 B2
(45) Date of Patent: Nov. 10, 2026

(54) INHIBITORS OF HISTONE ACETYLTRANSFERASE p300/CBP FOR CANCER THERAPY

(71) Applicant: BAYLOR COLLEGE OF MEDICINE, Houston, TX (US)

(72) Inventors: Yongcheng Song, Houston, TX (US); Fangrui Wu, Houston, TX (US); Shenyou Nie, Houston, TX (US); Yuanda Hua, Houston, TX (US); Yi-Lun Lin, Houston, TX (US); Salma Kaochar, Houston, TX (US); Nicholas Mitsiades, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 904 days.

(21) Appl. No.: 17/918,074

(22) PCT Filed: Apr. 8, 2021

(86) PCT No.: PCT/US2021/026348

§ 371 (c)(1),
(2) Date: Oct. 10, 2022

(87) PCT Pub. No.: WO2021/207469

PCT Pub. Date: Oct. 14, 2021

(65) Prior Publication Data

US 2023/0167101 A1 Jun. 1, 2023

Related U.S. Application Data

(60) Provisional application No. 63/007,711, filed on Apr. 9, 2020.

(51) Int. Cl.

| | |
|---|---|
| ***A61P 35/00*** | (2006.01) |
| ***C07D 333/20*** | (2006.01) |
| ***C07D 405/12*** | (2006.01) |
| ***C07D 405/14*** | (2006.01) |
| ***C07D 409/12*** | (2006.01) |
| ***C07D 409/14*** | (2006.01) |
| ***C07D 417/12*** | (2006.01) |

(52) U.S. Cl.

CPC ............ *C07D 409/12* (2013.01); *A61P 35/00* (2018.01); *C07D 333/20* (2013.01); *C07D 405/12* (2013.01); *C07D 405/14* (2013.01); *C07D 409/14* (2013.01); *C07D 417/12* (2013.01)

(58) Field of Classification Search

CPC ..... A61P 35/00; C07D 333/16; C07D 333/20; C07D 405/12; C07D 405/14; C07D 409/10; C07D 409/12; C07D 409/14; C07D 417/12

See application file for complete search history.

(56) References Cited

U.S. PATENT DOCUMENTS

| | | | | |
|---|---|---|---|---|
| 2006/0122229 | A1 | 6/2006 | Berggren et al. | |
| 2006/0264470 | A1* | 11/2006 | Barth | A61P 13/10 548/465 |
| 2011/0306539 | A1 | 12/2011 | Shen et al. | |
| 2018/0000821 | A1 | 1/2018 | Cheresh et al. | |

FOREIGN PATENT DOCUMENTS

| | | | | |
|---|---|---|---|---|
| WO | WO-2005033102 | A2 * | 4/2005 | A61P 37/06 |
| WO | WO-2006113704 | A2 * | 10/2006 | A61P 31/04 |
| WO | WO 2020/210428 | | 10/2020 | |
| WO | WO 2021/119447 | | 6/2021 | |
| WO | WO2021119447 | A1 | 6/2021 | |

OTHER PUBLICATIONS

Thiophene Derivatives as New Anticancer Agents and Their Therapeutic Delivery Using Folate Receptor-Targeting Nanocarriers M Zhao, Y Cui, L Zhao, T Zhu, RJ Lee, W Liao, F Sun, Y Li, and L Teng ACS Omega, vol. 4, Issue 5, pp. 8874-8880 (Year: 2019).*

"The effect of surface poly(ethylene glycol) length on in vivo drug delivery behaviors of polymeric nanoparticles" JL Wang et al. Biomaterials, vol. 182, pp. 104-113 (Year: 2018).*

Search Report for European Pat. App. No. 21784228.5, mailed on May 28, 2024.

Fangrui Wu et al, "3-(Piperidin-4-ylmethoxy)pyridine Containing Compounds Are Potent Inhibitors of Lysine Specific Demethylase 1", Journal of Medicinal Chemistry, vol. 59, No. 1, Jan. 14, 2016 (Jan. 14, 2016), pp. 253-263, XP055440785.

Wu Fangrui et al: "Discovery, Structure-Activity Relationship, and Biological Activity of Histone-Competitive Inhibitors of Histone Acetyltransferases P300/CBP", Journal of Medicinal Chemistry, vol. 63, No. 9, Apr. 21, 2020 (Apr. 21, 2020) , pp. 4716-4731, XP093141688.

Manzo F et al: "Histone acetyltransferase inhibitors and preclinical studies", Expert Opinion on Therapeutic Patents, Taylor & Francis, GB, vol. 19, No. 6, Jun. 1, 2009 (Jun. 1, 2009), pp. 761-774, XP002616149.

Stefano Vernarecci et al: "Tuning acetylated chromatin with HAT inhibitors: a novel tool for therapy", EPIGENETICS, vol. 5, No. 2, Feb. 16, 2010 (Feb. 16, 2010), pp. 105-111, XP55333750.

International Search Report for International Application No. PCT/US2021/026348, mailed on Aug. 24, 2021.

(Continued)

*Primary Examiner* — Kara R. McMillian
*Assistant Examiner* — Sophia P Hirakis
(74) *Attorney, Agent, or Firm* — Farhang Amini; Shackelford, McKinley & Norton, LLP

(57) ABSTRACT

Embodiments of the present disclosure pertain to compositions that include a compound that inhibits the histone acetyl transferase activity of a protein, such as p300 and/or CBP. Further embodiments of the present disclosure pertain to methods of inhibiting the histone acetyl transferase activity of a protein by exposing the protein to a composition that contains one or more of the compounds of the present disclosure. The compositions of the present disclosure may be exposed to a protein in vitro or in vivo. Additional embodiments of the present disclosure pertain to methods of treating a cancer in a subject by administering a composition of the present disclosure to the subject in order to treat the cancer.

5 Claims, 20 Drawing Sheets

(56) References Cited

OTHER PUBLICATIONS

PubChem-SID:383220112 Deposit Date: Apr. 26, 2019 (Apr. 26, 2019) pp. 1-6; p. 2.

Presentation entitled "Retinal Regeneration Through Epigeneic Therapy", Presented at the Therapeutic Innovation Center at Baylor College of Medicine on Dec. 16, 2019, Rui Chen, Ph.D.

* cited by examiner 1 (8.6 ± 0.4 μM)

2 (1.6 ± 0.2 μM)

3 (2.8 ± 0.6 μM)

4 (7.4 ± 0.8 μM)

5 (10.0 ± 1.4 μM)

6 (1.6 ± 0.2 μM)

7 (12% inhibition at 10 μM)

8 (36% inhibition at 10 μM)

9 (31% inhibition at 10 μM)

10 (7.4 ± 1.0 μM)

11 (1.7 ± 0.2 μM)

12 (0.62 ± 0.2 μM)

13 (0% inhibition at 10 μM)

14 (5.0 ± 1.6 μM)

15 (2.2 ± 0.4 μM)

16 (3.0 ± 1.0 μM)

17 (1.4 ± 0.3 µM)

18 (5% inhibition at 10 µM)

19 (20% inhibition at 10 µM)

20 R=Me (4.4 ± 1.6 µM)
21 R=CHO (7.0 ± 1.6 µM)

22 (5.4 ± 1.4 μM)

23 (10% inhibition at 10 μM)

24 (5.8 ± 0.6 μM)

25 (4.6 ± 1.4 μM)

26 (2.0 ± 0.5 μM)

27 (35% inhibition at 10 μM)

28 (0% inhibition at 10 μM)

29 (22% inhibition at 10 μM)

30 (23% inhibition at 10 µM)

31 (0% inhibition at 10 µM)

32 (18% inhibition at 10 µM)

33 (1.8 ± 0.3 µM)

34 (9.8 ± 2.4 μM)

35 (6.0 ± 0.6 μM)

36 (2.4 ± 0.6 μM)

37 (8.6 ± 2.6 μM)

38 (10% inhibition at 10 μM)

39 (18% inhibition at 10 μM)

SYC-1127 (2.3 μM)

| Control vs. Starved | Treated vs. Control | Cell proliferation related gene sets |
|---|---|---|
| 7.33 | -5.33 | HALLMARK_E2F TARGETS |
| 6.30 | -2.78 | HALLMARK_ESTROGEN_RESPONSE_LATE |
| 5.54 | -3.85 | HALLMARK G2M CHECK_POINT |
| 5.24 | -1.98 | HALLMA RK_ESTROGEN_RESPONSE_EARLY |
| 4.07 | -2.95 | HALLMARK_MYC_TARGETS_V1 |
| 489 | -3.75 | REACTOME_CELL_CYCLE_MITOTIC |
| 4.60 | -3.24 | REACTOME_DNA_STRAND_ELONGATION |
| 4.51 | -4.36 | REACTOME_CELL_CYCLE |
| 4.26 | -3.65 | REACTOME_DNA_REPLICATION |
| 3.75 | -2.88 | REACTOME_G2_M_CHECKPOINTS |
| 3.66 | -3.25 | REACTOME_MITOTIC_M_M_G1_PHASES |
| 3.52 | -2.20 | REACTOME_UNWINDING_OF_DNA |
| 3.36 | -2.59 | REACTOME_MITOTIC_G1_G1_S_PHASES |
| 3.36 | -2.41 | REACTOME_S_PHASE |
| 3.15 | -2.41 | REACTOME_G1_S_TRANSITION |
| 3.07 | -2.22 | REACTOME_SYNTHESIS_OF_DNA |
| 3.04 | -2.36 | REACTOME_DNA_REPAIR |

FIG. 7D

| Treated vs. Control | Upregulated gene sets in breast cancer patients |
|---|---|
| -4.658 | SOTIRIOU_BREAST_CANCER_GRADE_1_VS_3_UP |
| -3.186 | PUJANA_BREAST _CANCER_WITH_BRCA1_MUTATED_UP |
| -2.517 | SMID_BREAST_CANCER_BASAL_UP |
| -2.476 | POOLA_INVASIVE_BREAST_CANCER_UP |
| -2.463 | SMID_BREAST_CANCER_RELAPSE_IN_BONE_UP |
| -2.435 | NIKOLSKY_BREAST_CANCER_16P13_AMPLICON |
| -2.340 | SMID_BREAST_CANCER_LUMINAL_B_UP |
| -2.246 | FINETTI_BREAST_CANCER_KINOME_RED |
| -2.164 | VANTVEER_BREAST_CANCER_POOR_PROGNOSIS |
| -2.135 | PUJANA_BREAST_CANCER_LIT_INT_NETWORK |
| -2.060 | DOANE_BREAST_CANCER_ESR1_UP |
| -2.044 | YANG_BREAST_CANCER_ESR1_BULK_UP |
| -1.970 | FARMER_BREAST_CANCER_CLUSTER_2 |
| -1.825 | KRAS.600.LUNG.BREAST_UP.V1_UP |
| -1.807 | VANTVEER_BREAST_CANCER_ESR1_UP |
| -1.794 | SMID_BREAST CANCER_RELAPSE_IN_BRAIN_UP |
| -1.693 | CHARAFE_BREAST_CANCER_LUMINAL_ VS_MESENCHYMAL_UP |
| -1.610 | KRAS.BREAST_UP.V1_UP |
| -1.587 | TURASHVILI_BREAST_LOBULAR_CARCINOMA_VS_DUCTAL_NORMAL_DN |
| -1.584 | HONRADO_BREAST CANCER_BRCA1_VS_BRCA2 |
| -1.582 | NADERI_BREAST CANCER_PROGNOSIS_UP |
| -1.527 | NIKOLSKY BREAST CANCER_19Q13.1_AMPLICON |

FIG. 7E

INHIBITORS OF HISTONE ACETYLTRANSFERASE p300/CBP FOR CANCER THERAPY

CROSS-REFERENCE TO RELATED APPLICATIONS

This application claims priority to U.S. Provisional Patent Application No. 63/007,711, filed on Apr. 9, 2020. The entirety of the aforementioned application is incorporated herein by reference.

STATEMENT REGARDING FEDERALLY SPONSORED RESEARCH

This invention was made with government support under P50 CA186784 awarded by the National Institutes of Health. The government has certain rights in the invention.

BACKGROUND

Histone acetylases, such as human p300 (E1A binding protein p300) and its paralog CBP (CREB (cAMP-response element binding protein) binding protein), are essential for many transcription factor-mediated gene transcription programs. Furthermore, p300 and CBP may contribute to the progression of numerous cancers. However, current inhibitors of p300 and CBP suffer from numerous limitations. Numerous embodiments of the present disclosure aim to address the aforementioned limitations.

SUMMARY

In some embodiments, the present disclosure pertains to compositions that include a compound. In some embodiments, the compound includes a structure that includes, without limitation:

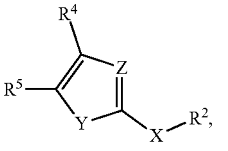

and

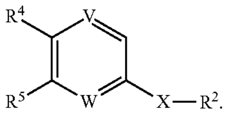

In some embodiments, the compounds of the present disclosure include the following structure:

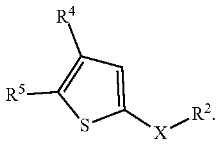

In some embodiments, the compounds of the present disclosure include the following structure:

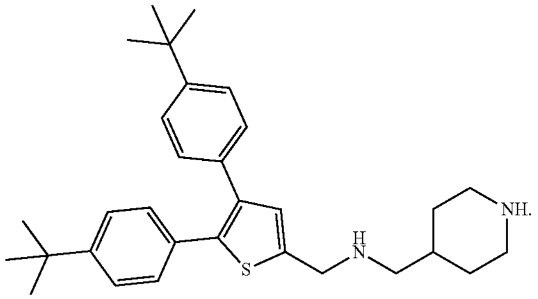 [SMILES: CC(C)(C)c1ccc(-c2cc(CNCC3CCNCC3)sc2-c2ccc(C(C)(C)C)cc2)cc1]

In some embodiments, the compounds of the present disclosure include the following structure:

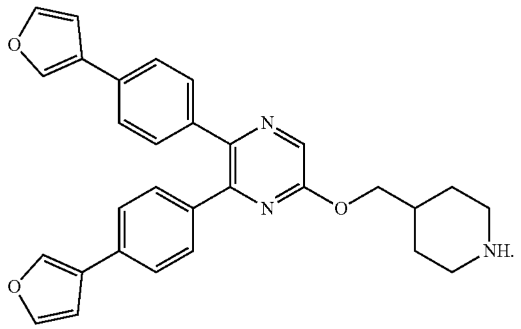 [SMILES: c1cc(-c2ccc(-c3ncc(OCC4CCNCC4)nc3-c3ccc(-c4ccoc4)cc3)cc2)co1]

In some embodiments, the compounds of the present disclosure can be used to inhibit the histone acetyl transferase activity of a protein. In some embodiments, the protein is p300. In some embodiments, the protein is CBP.

Additional embodiments of the present disclosure pertain to methods of inhibiting the histone acetyl transferase activity of a protein (e.g., p300 and/or CBP) by exposing the protein to a composition that contains one or more of the compounds of the present disclosure. In some embodiments, the compositions of the present disclosure may be exposed to a protein in vitro. As such, in some embodiments, the methods of the present disclosure can be utilized to study biological activity in vitro.

In some embodiments, the compositions of the present disclosure may be exposed to a protein in vivo in a subject. In some embodiments, the exposing occurs by administering the composition to the subject.

Additional embodiments of the present disclosure pertain to methods of treating a cancer in a subject by administering a composition of the present disclosure to the subject in order to treat the cancer. In some embodiments, the cancer to be treated includes, without limitation, cancers associated with p300 overexpression, cancers associated with CBP overexpression, and combinations thereof. In some embodiments, the cancer includes, without limitation, breast cancer, prostate cancer, pancreatic cancer, leukemia, acute myeloid leukemia, and combinations thereof. In some embodiments, the cancer is breast cancer.

DESCRIPTION OF THE DRAWINGS

FIGS. 4A-4B show plots of $IC_{50}$ values of compound 12 versus increasing concentrations of Ac-CoA (FIG. 4A) and histone H3 (FIG. 4B). The results suggest that compound 12 is non-competitive against Ac-CoA and competitive against histone. FIG. 4C shows alpha assay results demonstrating that compound 12 can dose-dependently disrupt the binding between p300 HAT and histone H4.

FIG. 5A shows 10 docking conformations of compound 12 with lowest energies in the crystal structure of p300-HAT (shown as an electrostatic surface) in complex with Ac-CoA (as a tube model). FIG. 5B shows the lowest energy docking conformation of compound 12 (as a ball-and-stick model) with surrounding residues and Ac-CoA. Hydrogen bonds are shown as dotted lines.

FIGS. 7A-E summarize gene set enrichment analysis (GSEA) results showing significant gene expression changes ($p<0.001$) in ER+MCF-7 cells by treatment with compound 12, as compared to the starved (without estradiol) or control (with estradiol) group. FIG. 7A summarizes results indicating that inhibitor treatment caused significant downregulation of genes that were suppressed by siRNA-mediated p300 knockdown (GSE31873). FIGS. 7B-7E summarize results showing that compound 12 counteracted estradiol in MCF-7 cells. Treatment with compound 12 significantly suppressed expression of genes that were upregulated by estradiol (FIG. 7B), and induced expression of genes that were downregulated by estradiol (FIGS. 7D-E). FIGS. 7D-7E show GSEA heatmaps of normalized enrichment scores (NES) for publicly available gene signatures (from the MSigDB database). FIG. 7D shows that inhibitor 12 caused significant downregulation of cancer-related gene sets that were induced by estradiol. FIG. 7E shows that inhibitor 12 suppressed expression of gene sets associated with breast cancer as well as the poor prognosis, progression, invasion and relapse of breast cancer.

DETAILED DESCRIPTION

Figure 1:
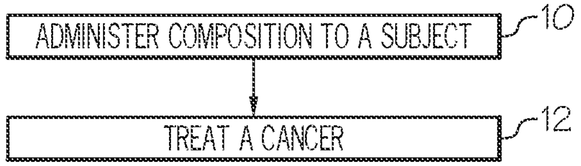
FIG. 1 illustrates a method of treating a cancer in a subject through the administration of the compositions of the present disclosure to the subject.
Figure 2A:
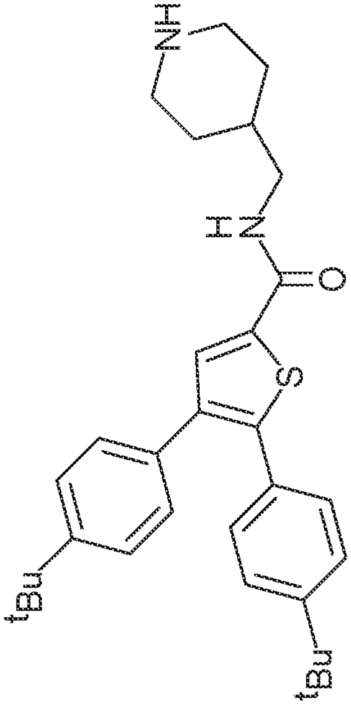
FIGS. 2A-2MM illustrate the structures of numerous compounds and their inhibitory activities against p300 HAT.
Figure 2B:
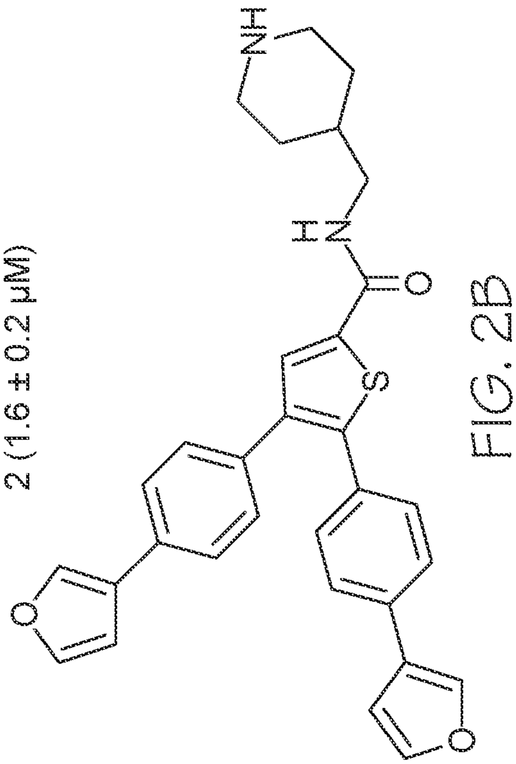
Figure 2C:
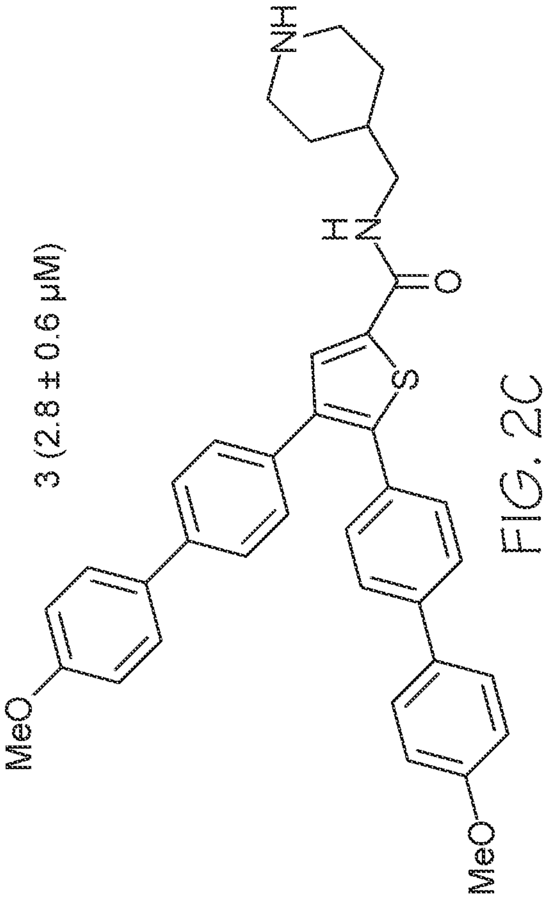
Figure 2D:
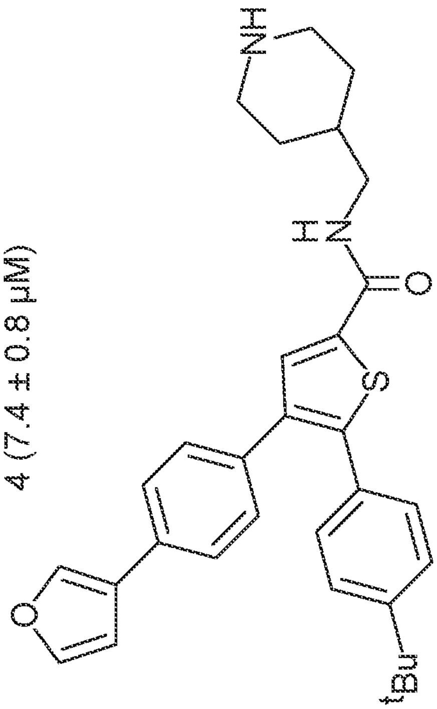
Figure 2E:
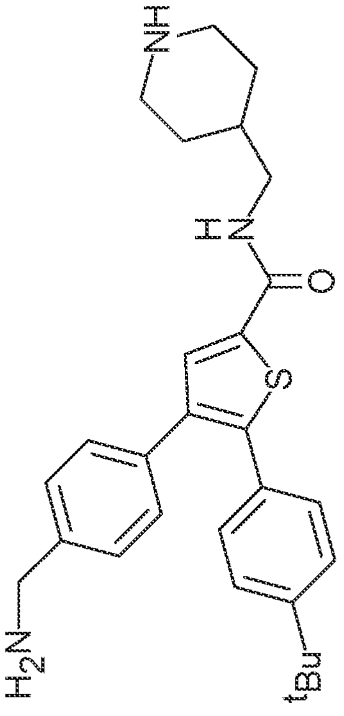
Figure 2F:
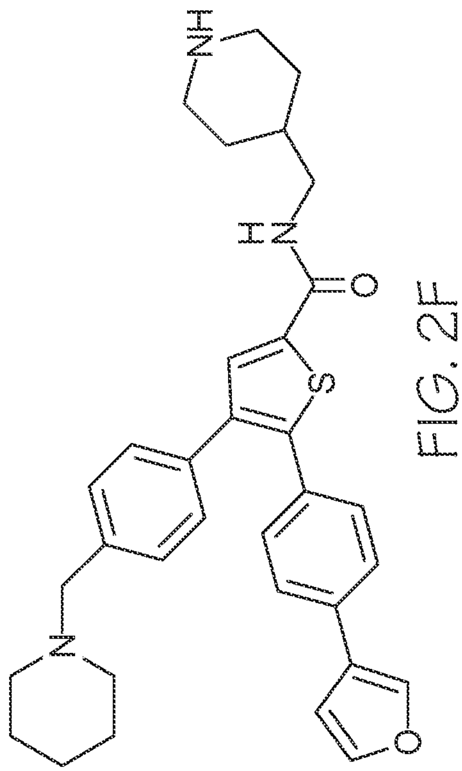
Figure 2G:
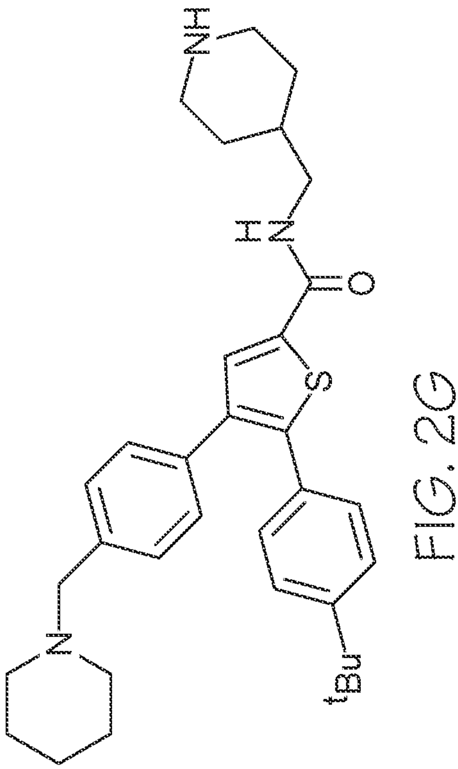
Figure 2H:
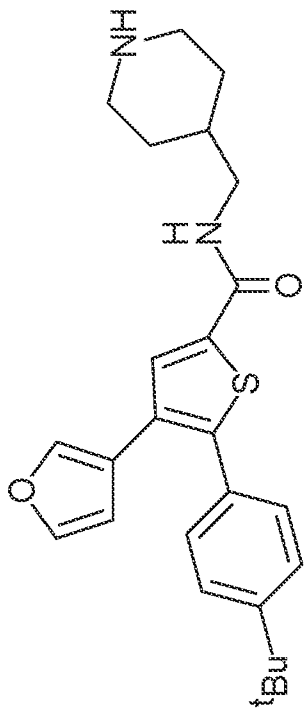
Figure 2I:
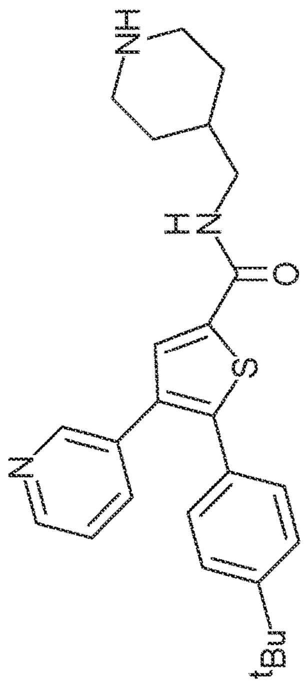
Figure 2J:
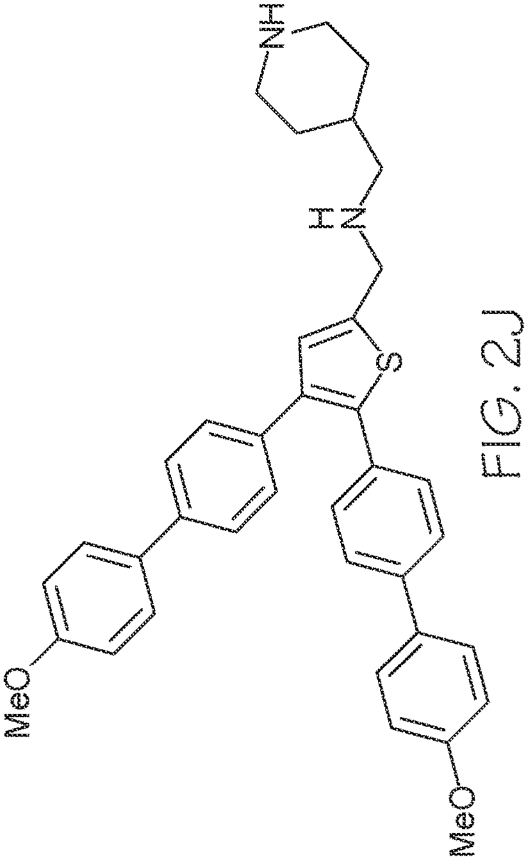
Figure 2K:
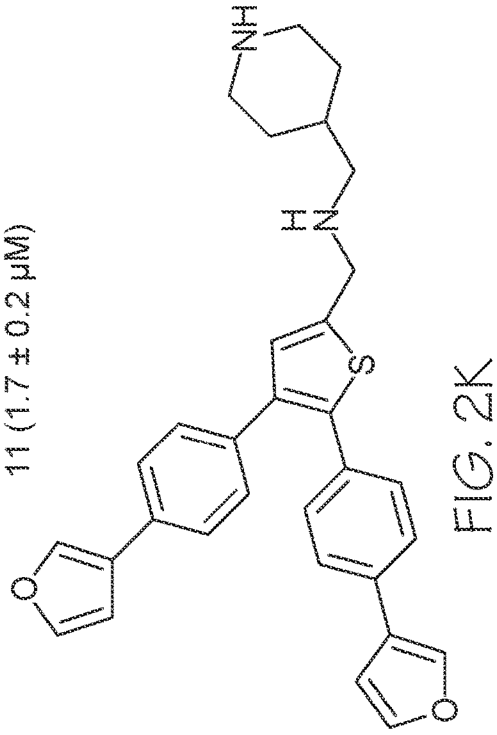
Figure 2L:
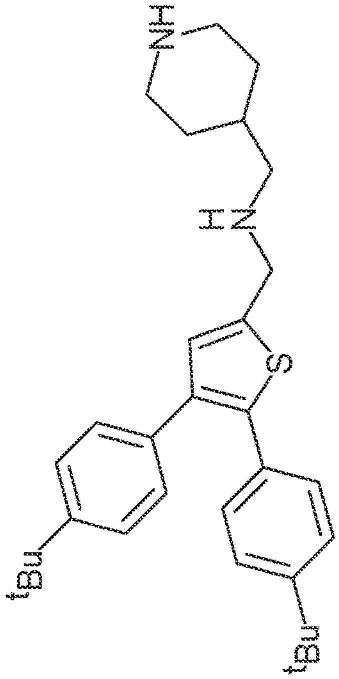
Figure 2M:
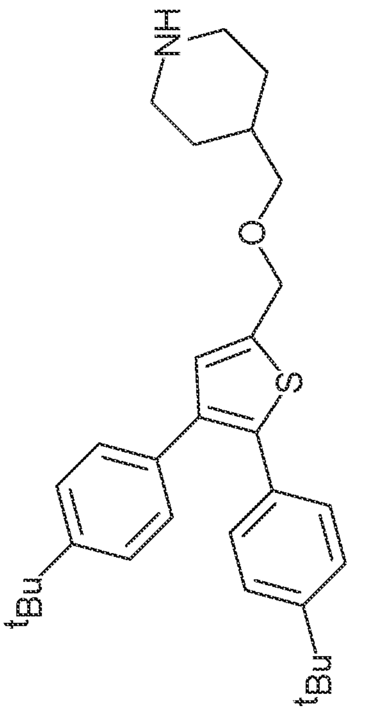
Figure 2N:
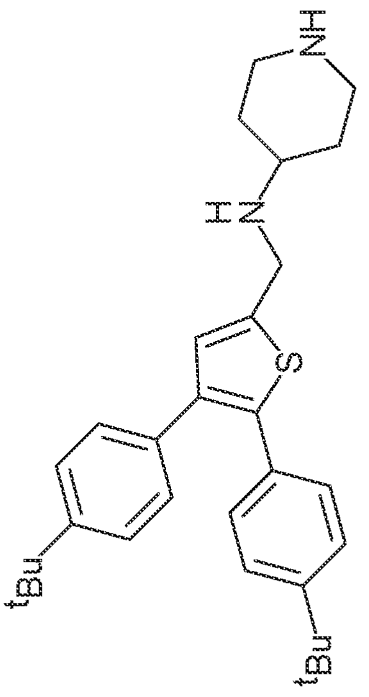
Figure 2O:
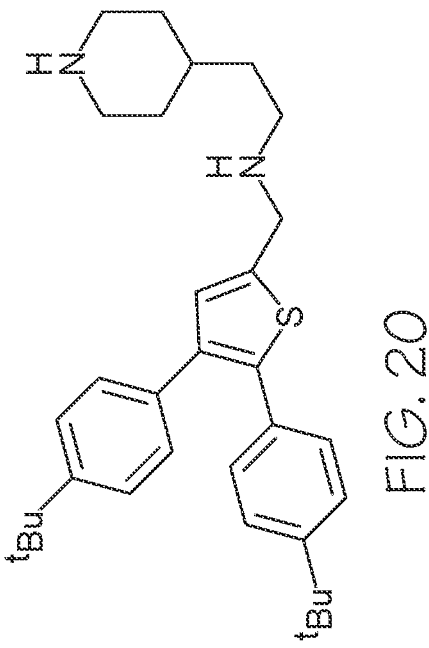
Figure 2P:
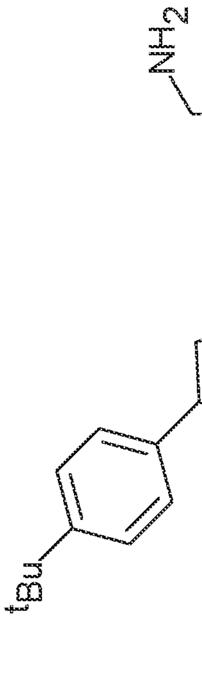
Figure 2Q:
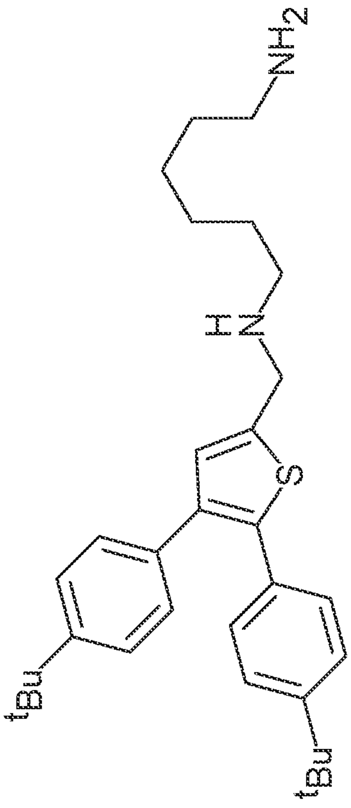
Figure 2R:
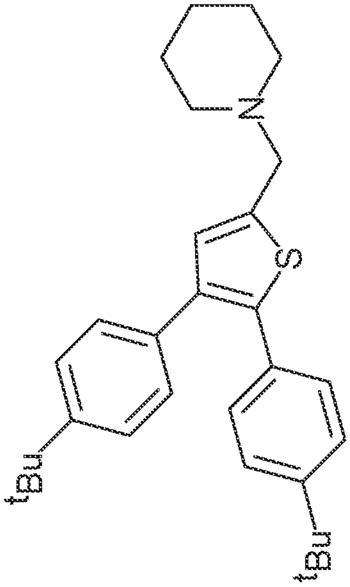
Figure 2S:
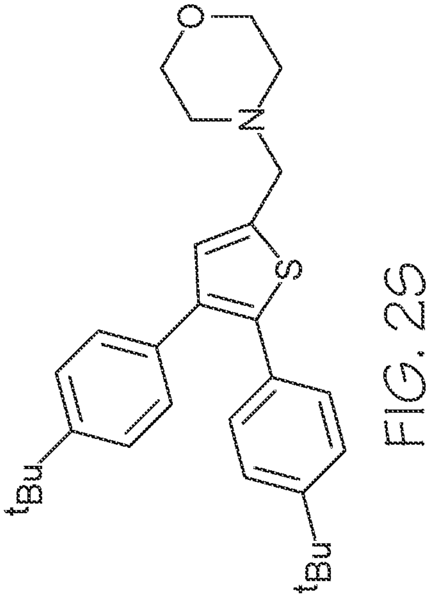
Figure 2T:
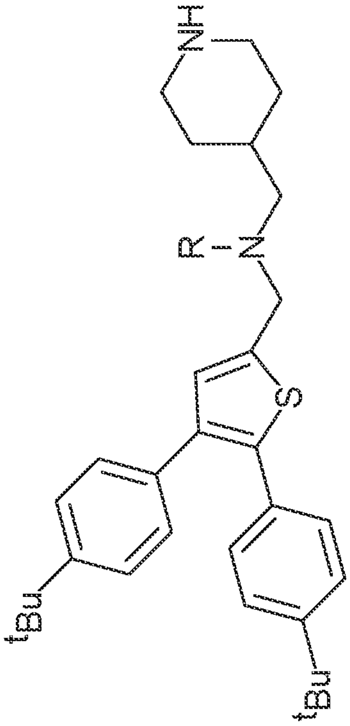
Figure 2U:
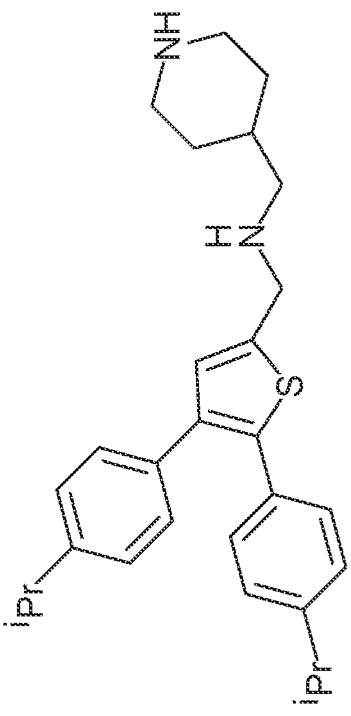
Figure 2V:
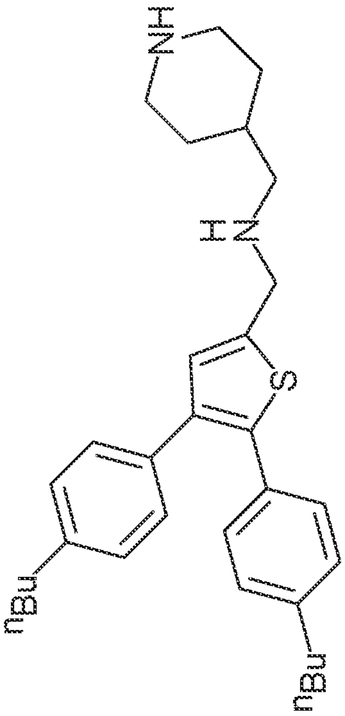
Figure 2W:
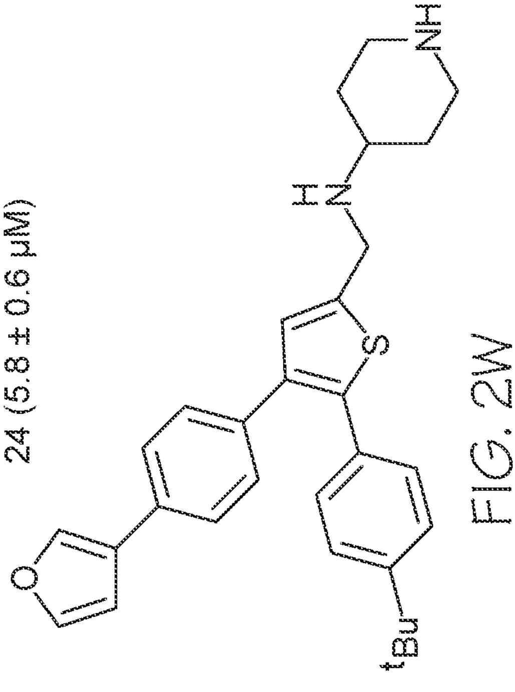
Figure 2X:
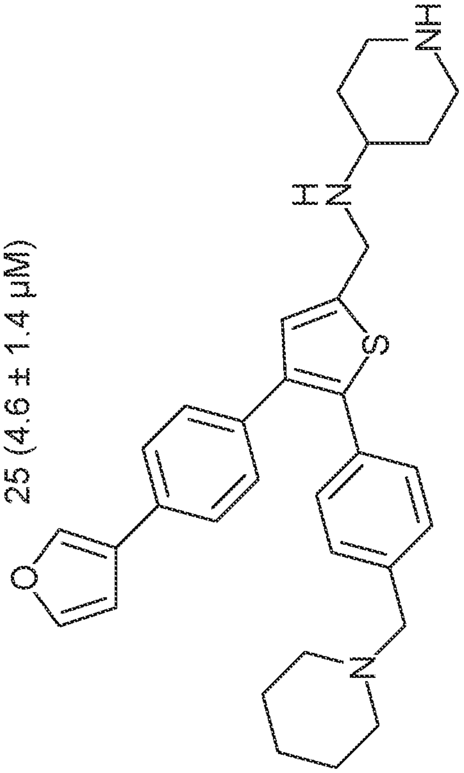
Figure 2Y:
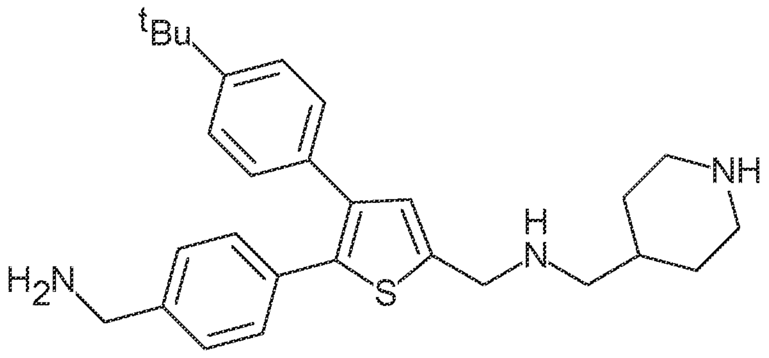
Figure 2Z:
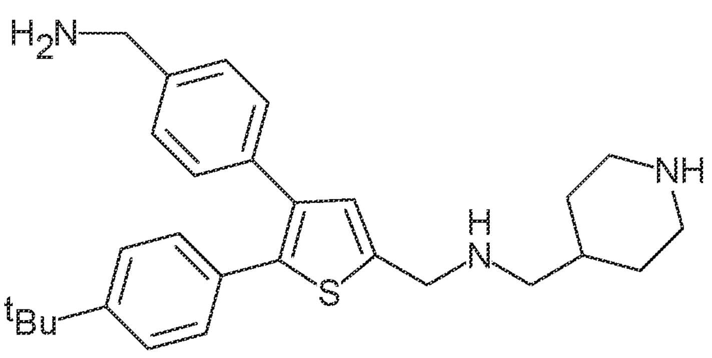
Figure 2A:
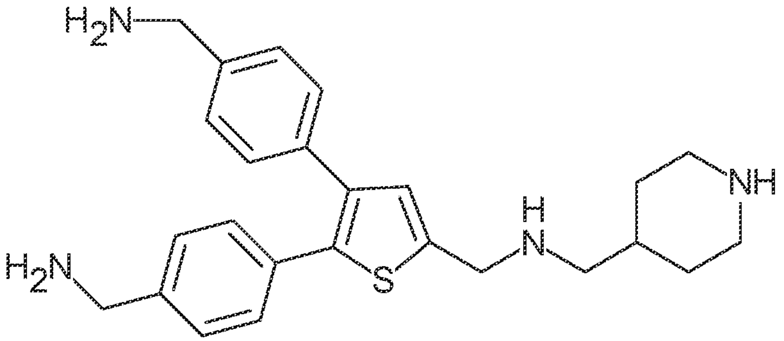
Figure 2B:
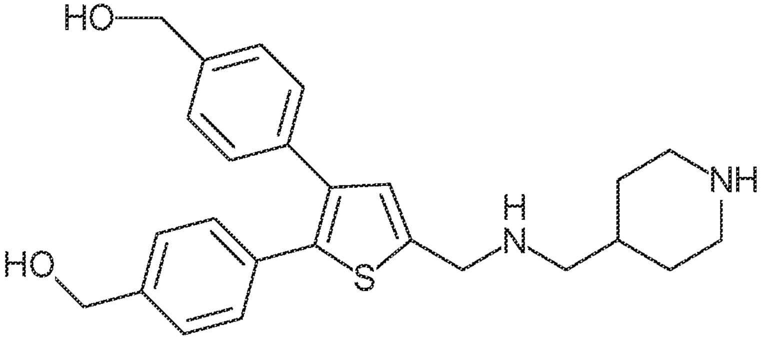
Figure 2C:
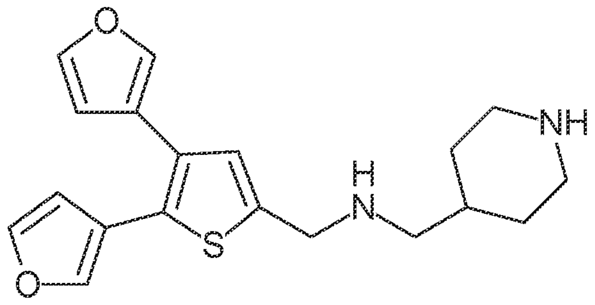
Figure 2D:
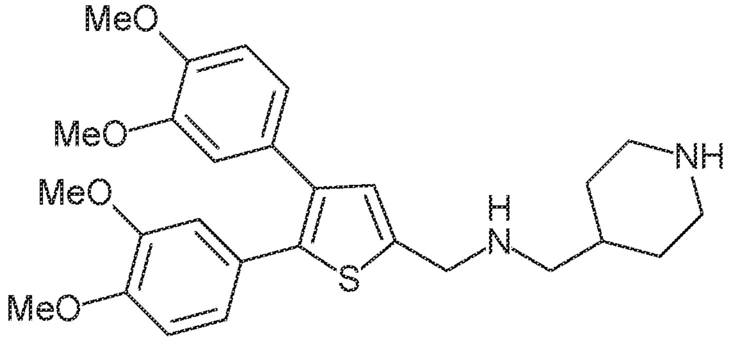
Figure 2E:
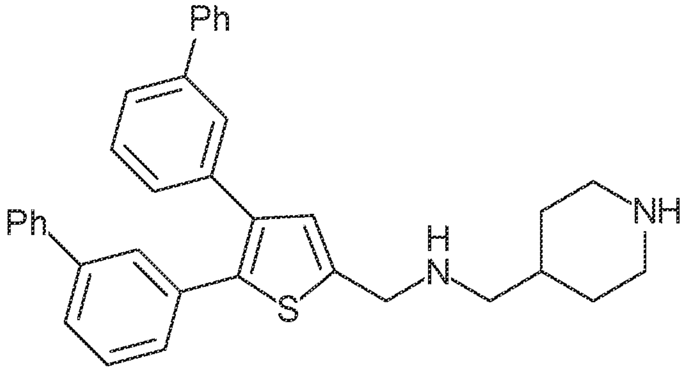
Figure 2F:
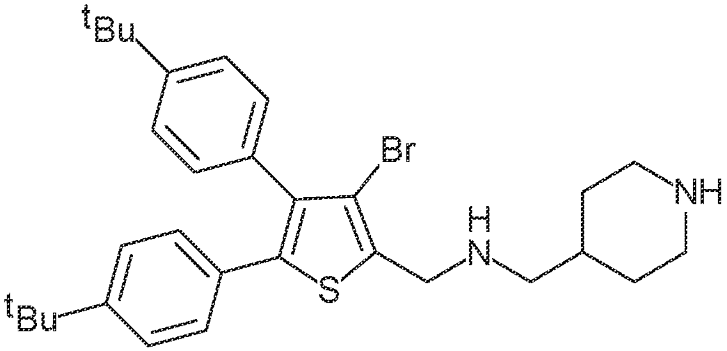
Figure 2G:
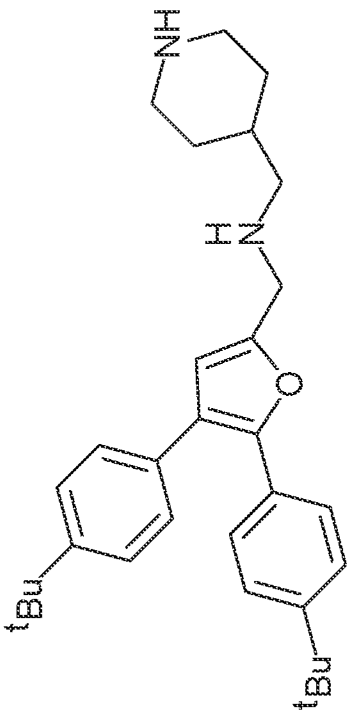
Figure 2H:
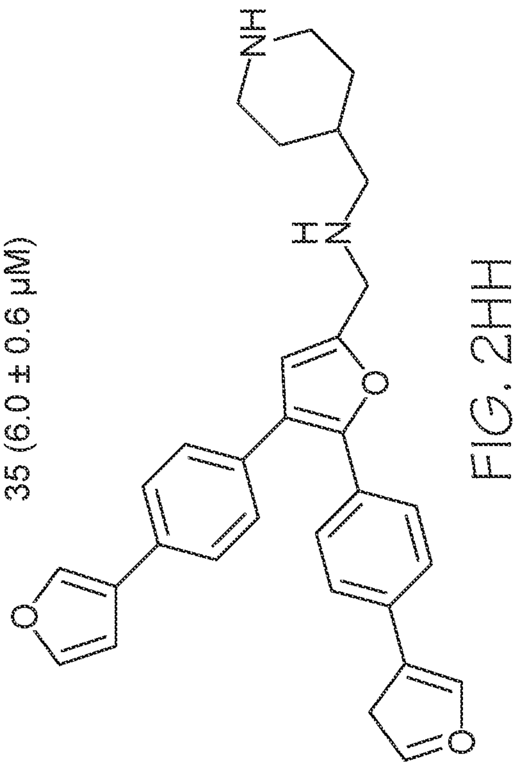
Figure 2I:
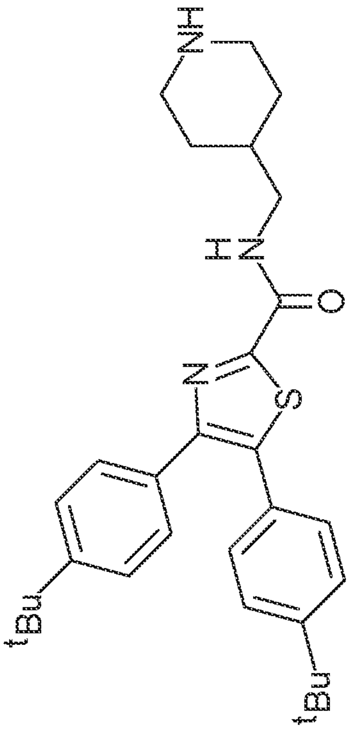
Figure 2J:
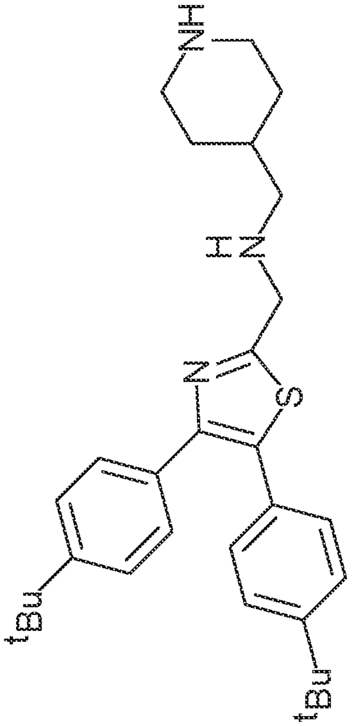
Figure 2K:
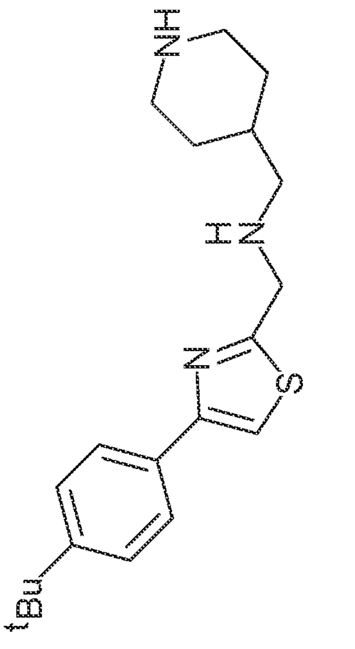
Figure 2L:
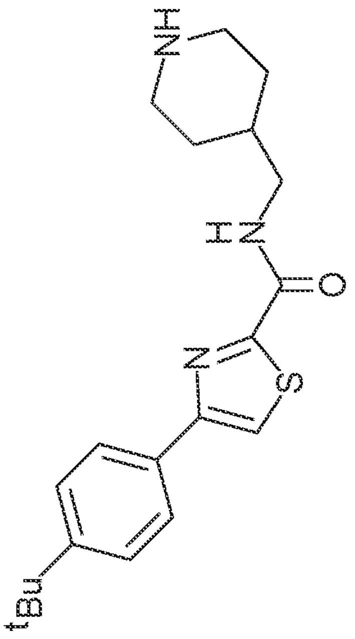
Figure 2M:
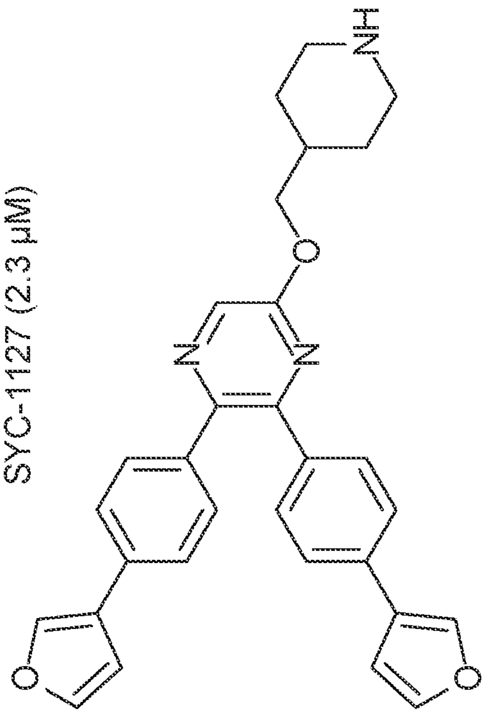

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Histone acetylation is one of the most important post-translational modifications. Acetylation of the sidechain amino group of a histone lysine residue neutralizes its positive charge (under physiological pH) and renders a more open DNA conformation to facilitate binding of transcription factors as well as other proteins for gene transcription, DNA replication and repair. In addition, acetylated lysine can be recognized by a number of proteins (such as bromodomain-containing proteins) and serve as an anchor point in chromatin to form a transcription complex that regulates gene expression.

Human p300 (E1A binding protein p300) and its paralog CBP (CREB (cAMP-response element binding protein) binding protein) are large proteins with ~2,400 amino acids, containing multiple structured domains including cysteine-histidine rich 1 (CH1), CREB-binding KIX, Bromodomain, histone acetyltransferase (HAT), CH3, and steroid receptor coactivator interaction (SID) domains. These structured domains, which share a high homology between p300 and CBP, are connected with less conserved intrinsically disordered regions (IDR).

The CH1, KIX, CH3 and SID domains as well as IDR of p300/CBP are transactivation domains, which interact with a number of transcription factors (e.g., CREB, p53 and HIF-1) and transcription coactivators (e.g., steroid receptor coactivators). Biologically, p300/CBP not only acetylates a lysine residue of histone (e.g., histone H3 lysine 27, or H3K27) and certain transcription factors (e.g., p53 and c-Myc), it also serves as a hub protein to link and stabilize a transcription complex.

Previous studies have shown that HAT activity of p300/CBP is essential for many transcription factor-mediated gene transcription programs. For example, estrogen receptor (ER) or androgen receptor (AR) mediated gene transcription pathway is of importance in female or male development as well as in breast or prostate cancer, respectively. HAT activity of p300 has been found to be required for ER- or AR-mediated gene expression. In addition, HAT of p300/CBP is a potential drug target for cancer therapy. Although there have been debates on whether p300/CBP alone is a tumor suppressor or an oncogene, convincing evidence has shown that p300/CBP HAT is essential for breast and prostate cancer as well as other cancers with p300 overexpression or harboring a p300/CBP fusion oncogene.

To date, several chemotypes of p300/CBP HAT inhibitors have been reported. However, except for recently disclosed compound A-485, other compounds are not good probes for cellular or in vivo studies. For instance, many p300/CBP HAT inhibitors suffer from limited cell permeability or efficacy, which render them unfavorable for drug development or cell biology.

As such, a need exists for the development of more effective inhibitors of p300 and CBP for numerous applications, including applications as chemical probes for biological studies of p300/CBP and cancer therapeutics. Numerous embodiments of the present disclosure address the aforementioned needs.

Compositions

In some embodiments, the present disclosure pertains to compositions that include a compound. In some embodiments, the compound includes a structure that includes, without limitation:

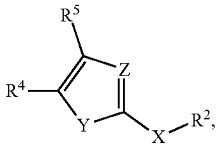 and 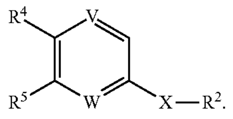

The structures of the compounds of the present disclosure can include numerous functional groups. For instance, in some embodiments, $R_2$, $R_4$, and $R_5$ can each independently include, without limitation, hydrogen, aromatic groups, phenyl groups, benzyl, furan groups, furanylphenyl groups, pyridine groups, pyridinylphenyl groups, biphenyl groups, piperidinylphenyl groups, pyrazole groups, piperidine groups, amine groups, alkyl amine groups, phenyl amine groups, phenyl alkyl amine groups, aniline groups, methyl piperidine groups, benzene groups, cyclohexane groups, methyl benzoate groups, benzyl piperidine groups, imidazole groups, piperidine amine groups, cyclic amine groups, cyclic aliphatic amine groups, cyclic piperidine-containing groups, 4-tertiary-butyl-phenyl (4-t-Bu-Ph), 4-isopropylphenyl (4-i-Pr-Ph), 4-Bu-Ph, 4-(furan-3-yl)-Ph, 4-methoxybiphenyl, 4-aminomethyl-Ph, 4-hydroxymethyl-Ph, piperidin-4-yl, piperidin-4-ylmethyl, 2-(piperidin-4-yl) ethyl, 4-(piperidin-1-ylmethyl)-Ph, piperazin-1-yl, 4-(piperazin-1-ylmethyl)-Ph, furan-3-yl, pyridin-3-yl, 4-methoxybiphenyl, 4-(furan-3-yl)-Ph, 3,4-dimethoxy-Ph, 3-biphenyl, 3-aminopropyl, 6-aminohexyl, morpholin-4-yl, derivatives thereof, and combinations thereof.

In some embodiments, Y includes, without limitation, S, O, NH, N-A, $CH_2$, and CHA. In some embodiments, A represents a functional group. In some embodiments, the functional group includes, without limitation, alkyl groups, alkene groups, alkyne groups, amide groups, amine groups, alkyl amine groups, alkyl amide groups, ether groups, ester groups, halogens (e.g., Br), derivatives thereof, and combinations thereof. In some embodiments, Y is S. In some embodiments, Y is O.

In some embodiments, Z, V and W each include, without limitation, N, CH, and CA. In some embodiments, X includes, without limitation, alkyl groups, alkene groups, alkyne groups, amide groups, amine groups, alkyl amine groups, alkyl amide groups, ether groups, ester groups, O, CONH, $CH_2NH$, $CH_2O$, $CH_2$, $CH_2N(Me)$, $CH_2N(CHO)$, derivatives thereof, and combinations thereof.

In some embodiments, $R_4$ includes, without limitation, hydrogen, aromatic groups, phenyl groups, benzyl, furan groups, furanylphenyl groups, pyridine groups, biphenyl groups, piperidinylphenyl groups, piperidine groups, phenyl amine groups, phenyl alkyl amine groups, benzene groups, benzyl piperidine groups, piperidine amine groups, 4-t-Bu-Ph, 4-i-Pr-Ph, 4-Bu-Ph, 4-(furan-3-yl)-Ph, 4-methoxybiphenyl, 4-aminomethyl-Ph, 4-hydroxymethyl-Ph, 4-(piperidin-1-ylmethyl)-Ph, piperazin-1-yl, 4-(piperazin-1-ylmethyl)-Ph, furan-3-yl, pyridin-3-yl, 4-methoxybiphenyl, 4-(furan-3-yl)-Ph, 3,4-dimethoxy-Ph, 3-biphenyl, derivatives thereof, and combinations thereof.

In some embodiments, $R_5$ includes, without limitation, hydrogen, aromatic groups, phenyl groups, benzyl, furan groups, furanylphenyl groups, pyridine groups, pyridinylphenyl groups, biphenyl groups, piperidinylphenyl groups, piperidine groups, phenyl amine groups, phenyl alkyl amine groups, benzene groups, benzyl piperidine groups, piperidine amine groups, 4-t-Bu-Ph, 4-i-Pr-Ph, 4-Bu-Ph, 4-(furan-3-yl)-Ph, 4-methoxybiphenyl, 4-aminomethyl-Ph, 4-hydroxymethyl-Ph, 4-(piperidin-1-ylmethyl)-Ph, piperazin-1-yl, 4-(piperazin-1-ylmethyl)-Ph, furan-3-yl, pyridin-3-yl, 4-methoxybiphenyl, 4-(furan-3-yl)-Ph, 3,4-dimethoxy-Ph, 3-biphenyl, derivatives thereof, and combinations thereof.

In some embodiments, X includes, without limitation, alkyl groups, amide groups, amine groups, alkyl amine groups, alkyl amide groups, ether groups, CONH, $CH_2NH$, $CH_2O$, $CH_2$, $CH_2N(Me)$, $CH_2N(CHO)$, derivatives thereof, and combinations thereof.

In some embodiments, $R_2$ includes, without limitation, piperidine groups, amine groups, alkyl amine groups, methyl piperidine groups, cyclohexane groups, piperidine amine groups, cyclic amine groups, cyclic aliphatic amine groups, cyclic piperidine-containing groups, piperidin-4-yl, piperidin-4-ylmethyl, 2-(piperidin-4-yl)ethyl, piperazin-1-yl, 3-aminopropyl, 6-aminohexyl, morpholin-4-yl, derivatives thereof, and combinations thereof.

In some embodiments, Y is S or O. In some embodiments, Z is N or CH. In some embodiments, V is N. In some embodiments, W is N.

In some embodiments, the compounds of the present disclosure include the following structure:

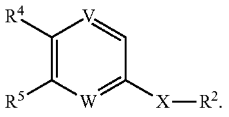

In some embodiments, the compounds of the present disclosure include the following structure:

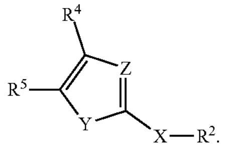

In some embodiments, the compounds of the present disclosure include the following structure:

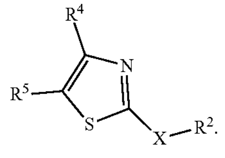

In some embodiments, each of $R_4$ and $R_5$ in the aforementioned structure independently includes, without limitation, 4-t-Bu-Ph, 4-i-Pr-Ph, and derivatives thereof. In some embodiments, X in the aforementioned structure includes, without limitation, CONH, $CH_2NH$, and derivatives thereof. In some embodiments, $R_2$ in the aforementioned structure includes piperidine groups, amine groups, alkyl amine groups, methyl piperidine groups, cyclohexane groups, piperidine amine groups, cyclic amine groups, cyclic aliphatic amine groups, cyclic piperidine-containing groups, piperidin-4-yl, piperidin-4-ylmethyl, 2-(piperidin-4-yl)ethyl, derivatives thereof, and combinations thereof.

In more specific embodiments, the compounds of the present disclosure include, without limitation, one or more of structures listed in FIGS. 2A-2MM.

In some embodiments, the compounds of the present disclosure include the following structure:

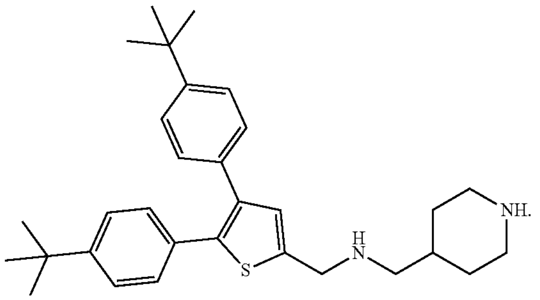 [SMILES: CC(C)(C)c1ccc(-c2cc(CNCC3CCNCC3)sc2-c2ccc(C(C)(C)C)cc2)cc1]

In some embodiments, the compounds of the present disclosure include the following structure:

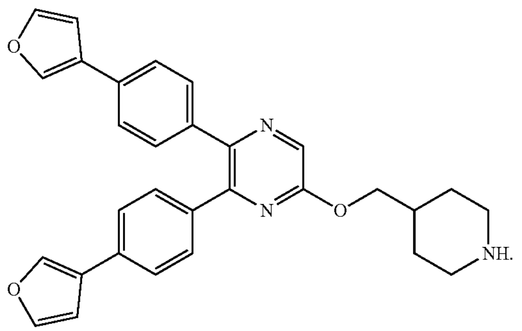 [SMILES: c1cc(-c2ccc(-c3ncc(OCC4CCNCC4)nc3-c3ccc(-c4ccoc4)cc3)cc2)co1]

The compounds of the present disclosure have various advantageous properties and uses. For instance, in some embodiments, the compounds of the present disclosure inhibit the histone acetyl transferase activity of a protein. As such, in some embodiments, the compounds of the present disclosure can be used to inhibit the histone acetyl transferase activity of a protein. In some embodiments, the protein is E1A binding protein p300 (p300). In some embodiments, the protein is CREB (cAMP-response element binding protein) binding protein (CBP).

In some embodiments, the compounds of the present disclosure are competitive inhibitors of the histone acetyl transferase activity of a protein. In some embodiments, the compounds of the present disclosure are selective inhibitors of the histone acetyl transferase activity of a protein.

In some embodiments, the compounds of the present disclosure inhibit the histone acetyl transferase activity of a protein with an $IC_{50}$ value ranging from 500 nm to 15 μM. In some embodiments, the compounds of the present disclosure inhibit the histone acetyl transferase activity of a protein with an $IC_{50}$ value ranging from 500 nm to 5 μM. In some embodiments, the compounds of the present disclosure inhibit the histone acetyl transferase activity of a protein with an $IC_{50}$ value ranging from 500 nm to 2 μM. In some embodiments, the compounds of the present disclosure inhibit the histone acetyl transferase activity of a protein with an $IC_{50}$ value ranging from 500 nm to 1 μM. In some embodiments, the compounds of the present disclosure inhibit the histone acetyl transferase activity of a protein with an $IC_{50}$ value of 620 nm.

Compositions that contain the compounds of the present disclosure may be in various forms. For instance, in some embodiments, the composition is associated with a delivery agent, such as a nanoparticle.

In some embodiments, the compositions of the present disclosure include at least one excipient agent. In some embodiments, the at least one excipient agent includes, without limitation, anti-adherents, binders, coatings, colors, disintegrants, flavors, glidants, lubricants, preservatives, sorbents, sweeteners, vehicles, or combinations thereof.

In some embodiments, the compositions of the present disclosure include at least one solubilizing agent. In some embodiments, the at least one solubilizing agent includes, without limitation, polyethylene glycol, glycerin, propylene glycol, ethanol, sorbitol, polyoxyethylated glycerides, polyoxyethylated oleic glycerides, polysorbates, sorbitan monooleate, hydroxypropyl-beta-cyclodextrin (HPCD), polyoxyl 40 hydrogenated castor oil, polyoxyl hydroxystearates, or combinations thereof.

Methods of Inhibiting Histone Acetyl Transferase Activities of a Protein

Additional embodiments of the present disclosure pertain to methods of inhibiting the histone acetyl transferase activity of a protein. In some embodiments, the methods of the present disclosure include a step of exposing the protein to a composition that contains one or more of the compounds of the present disclosure.

In some embodiments, the methods of the present disclosure can be utilized to inhibit the histone acetyl transferase activity of p300. In some embodiments, the methods of the present disclosure can be utilized to inhibit the histone acetyl transferase activity of CBP.

In some embodiments, the compositions of the present disclosure may be exposed to a protein in vitro. As such, in some embodiments, the methods of the present disclosure can have various advantageous in vitro applications. For instance, in some embodiments, the methods of the present disclosure can be utilized to study biological activity in vitro. In more specific embodiments, the compounds of the present disclosure can be utilized as probes to study the enzymatic activity of proteins in vitro.

In some embodiments, the compositions of the present disclosure may be exposed to a protein in vivo in a subject. In some embodiments, the exposing occurs by administering the composition to the subject. In some embodiments, the administering is performed by a method that includes, without limitation, oral administration, inhalation, subcutaneous administration, intravenous administration, intra-nasal administration, intra-dermal administration, trans-dermal administration, intraperitoneal administration, intramuscular administration, intrathecal injection, topical administration, central administration, peripheral administration, trans-dermal administration, intraarterial administration, intracranial administration, intraspinal administration, intranasal administration, intraocular administration, intratumor administration, intramuscular administration, intranasal administration, subcutaneous administration, intra- or trans-dermal administration, intravenous administration, topical administration, or combinations thereof.

The compositions of the present disclosure may be administered to various subjects. For instance, in some embodiments, the subject is a human being. In some embodiments, the subject is suffering from cancer. In some embodiments, the cancer includes, without limitation, cancers associated with p300 overexpression, cancers associated with CBP overexpression, and combinations thereof. In some embodiments, the cancer includes, without limitation, breast cancer, prostate cancer, pancreatic cancer, leukemia, acute myeloid leukemia, and combinations thereof. In some embodiments, the cancer includes breast cancer.

The methods of the present disclosure can have various advantageous in vivo applications. For instance, in some embodiments, the methods of the present disclosure may be utilized to treat a cancer in a subject. In some embodiments, the methods of the present disclosure can be utilizes as in vivo probes to study the biological activity of cells.

Methods of Treating Cancer

Additional embodiments of the present disclosure pertain to methods of treating a cancer in a subject. In some embodiments illustrated in FIG. 1, the methods of the present disclosure include administering a composition of the present disclosure to the subject (step 10) in order to treat the cancer (step 12).

In some embodiments, the compositions of the present disclosure are administered through routes that include, without limitation, oral administration, inhalation, subcutaneous administration, intravenous administration, intra-nasal administration, intra-dermal administration, trans-dermal administration, intraperitoneal administration, intramuscular administration, intrathecal injection, topical administration, central administration, peripheral administration, transdermal administration, intraarterial administration, intracranial administration, intraspinal administration, intranasal administration, intraocular administration, intratumor administration, intramuscular administration, intranasal administration, subcutaneous administration, intra- or trans-dermal administration, intravenous administration, topical administration, or combinations thereof.

The methods of the present disclosure can be utilized to treat cancer in numerous subjects. For instance, in some embodiments, the subject is a human being.

The methods of the present disclosure can be utilized to treat numerous types of cancer. For instance, in some embodiments, the cancer includes, without limitation, cancers associated with p300 overexpression, cancers associated with CBP overexpression, and combinations thereof. In some embodiments, the cancer includes, without limitation, breast cancer, prostate cancer, pancreatic cancer, leukemia, acute myeloid leukemia, and combinations thereof. In some embodiments, the cancer is breast cancer.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Discovery and Biological Activity of Histone-Competitive Inhibitors of Histone Acetyltransferases P300/CBP Histone acetyltransferase (HAT) p300 and its paralog CBP acetylate histone lysine sidechains play critical roles in regulating gene transcription. The HAT domain of p300/CBP is also a potential drug target for cancer. In this Example, Applicant disclose small-molecule inhibitors of p300/CBP HAT. Biochemical and cell-based biological assays were performed to characterize the activities of these compounds.

A novel series of small molecule inhibitors of p300/CBP HAT with $IC_{50}$ values as low as 620 nM were discovered and characterized. The most potent inhibitor was found to be competitive against the substrate histone, showing a different mode of action from previously reported inhibitors. The inhibitor exhibited a high selectivity for p300/CBP, without significant activity against two other classes of HATs in human. The molecule inhibited cellular acetylation of several histone lysine residues and had strong activity with $EC_{50}$ of 1-3 μM against proliferation of several tumor cell lines in which p300 HAT is of importance.

Gene expression profiling in estrogen receptor (ER)-positive breast cancer MCF-7 cells showed that treatment with the inhibitor recapitulated siRNA-mediated p300 knockdown, inhibited ER-mediated gene transcription, and suppressed expression of numerous cancer-related gene signatures. The results in this Example demonstrate that the small molecule inhibitor are not only a useful probe for biological studies of p300/CBP HAT, but also a pharmacological lead for further drug development targeting cancer.

Example 1.1. Inhibitor Discovery

Applicant reports the discovery, structure activity relationships (SAR), biochemical and biological activities of a novel series of small molecule inhibitors of p300/CBP HAT that are competitive against the histone substrate. A biochemical assay to determine the activity and inhibition of recombinant HAT domain of human p300 was developed, using the substrate histone H3 (1-21) peptide and the $^3$H-labeled cofactor Ac-CoA.

Applicant screened a proprietary compound library containing ~300 compounds, which were synthesized during the past few years for structure-activity relationship (SAR) studies of lysine specific demethylase 1 (LSD1), whose substrate is methylated histone H3 lysine 4 (H3K4). Thiophene-2-carbamide compound 1 (FIG. 2A) was found to be a novel inhibitor of p300 HAT with $IC_{50}$ (concentration at which the enzyme activity is inhibited by 50%) value of 8.6 μM.

Example 1.2. Synthesis

Figure 3:
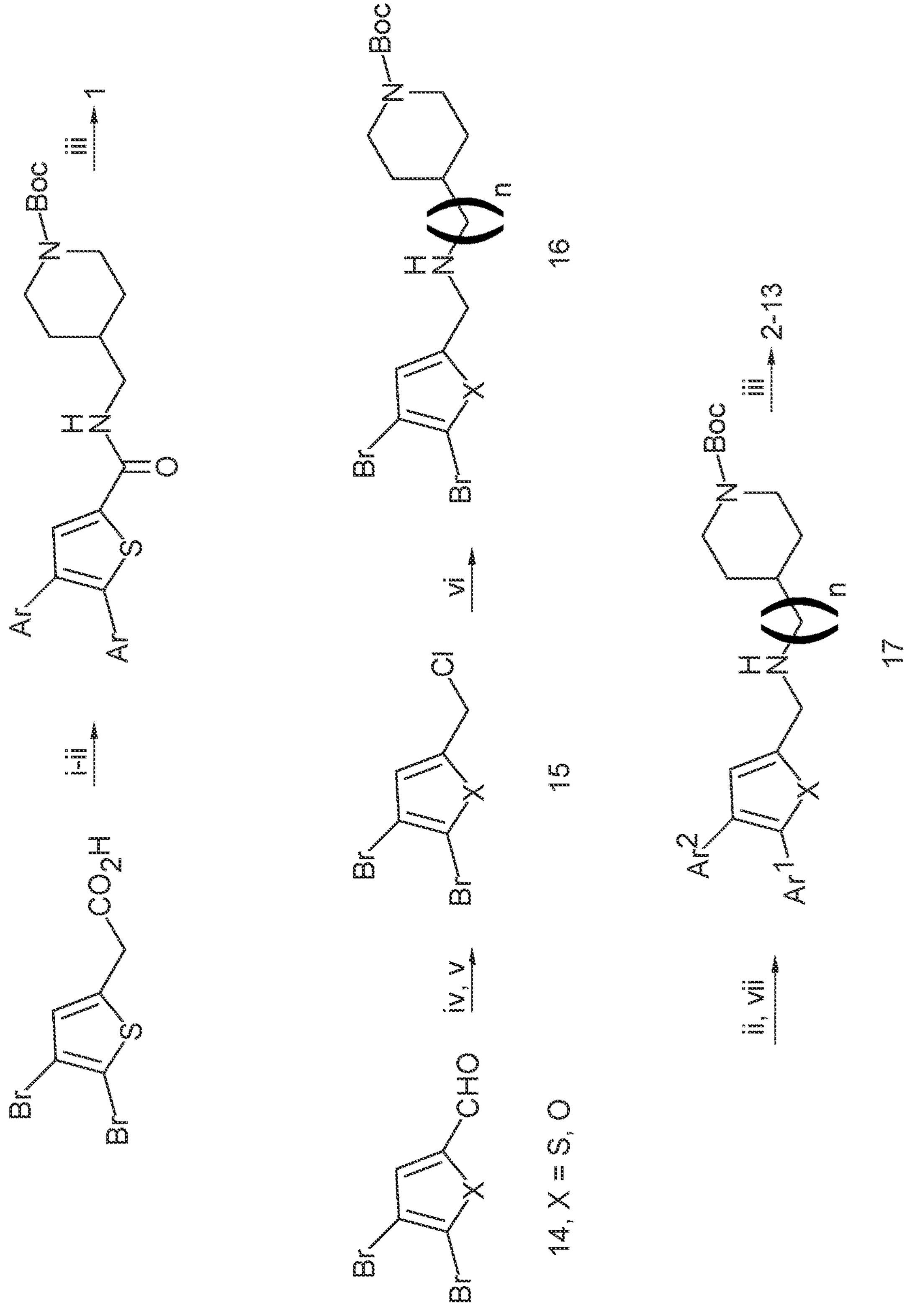
FIG. 3 provide general synthetic methods for the compounds in FIGS. 2A-2MM. Reagents and conditions: (i) 1-ethyl-3-(3-dimethylaminopropyl)carbodiimide, 1-hydroxybenzotriazole, 4-(aminomethyl)-1-BOC-piperidine, $CH_2Cl_2$, 96% yield; (ii) Ar—$B(OH)_2$, $Pd(PPh_3)_4$, $Na_2CO_3$, 80° C., 80-90% yield; (iii) HCl in 1,4-dioxane, >90% yield; (iv) $NaBH_4$, MeOH; (v) cyanuric chloride, DMF, 81% yield for the 2 steps; (vi) 4-(aminomethyl)-1-BOC-piperidine or other amine analogs, $K_2CO_3$, DMF, 60-85% yield; (vii) Ar—$B(OH)_2$, $Pd(PPh_3)_4$, $Na_2CO_3$, 100° C., 80-90% yield.

More derivatives of compound 1 were synthesized and tested for their activities against p300 HAT. General methods for synthesis of the compounds in FIGS. 2A-2MM are shown in FIG. 3. Synthesis of compound 1 was started with a standard amide formation reaction between 4,5-dibromothiophene-2-carboxylic acid and 1-tert-butyloxycarbonyl (BOC) protected 4-(aminomethyl)piperidine. The 5-and 4-Br groups of the amide thus obtained can undergo two Suzuki coupling reactions to give, upon deprotection of BOC, compound 1. For compounds 11-16 and 20-23, the 2-CHO group of 4,5-dibromothiophene-2-carbaldehyde (14, X═S) was reduced to an alcohol, followed by conversion to —$CH_2Cl$ by treatment with cyanuric chloride. The —Cl of the product 15 was substituted with an amine and the resulting compound 16 was subjected to two Suzuki coupling reactions with different aryl boronic acids with a high selectivity (23): 5-Br was reacted first at a lower temperature of 80° C., followed by 4-Br at 100° C. Upon deprotection of BOC, the target thiophene compounds 11-16 and 20-23 were obtained. Compound 34 was synthesized similarly from the furan 14 (X═O).

Example 1.3. Structure-Activity Relationship

Structures and inhibitory activities against p300 HAT of 13 representative compounds are shown in FIG. 3. Compound 12 by replacing the amide (—CONH—) group in the 2-substituent of 1 with a secondary amine (—$CH_2NH$—) linkage was found to be a potent inhibitor with an $IC_{50}$ of 620 nM, while changing to a —$CH_2O$— linkage in compound 13 resulted in a complete loss of inhibitory activity. Compound 14 or 15, whose 2-substituent is one —$CH_2$— shorter or longer than that of compound 12, respectively, was found to possess ~8-or 3-fold activity reduction ($IC_{50}$=5.0 or 2.2 μM). Compound 16 with a linear 2-sidechain showed significantly reduced inhibitory activity ($IC_{50}$=3.0 μM), as compared to compound 12 with a more hydrophobic, cyclic piperidine-containing group. Loss of activity for a compound bearing a shorter piperazine ring suggests a longer and cyclic amine such as that in compound 12 is more favored. Moreover, methylation and formylation of the middle —NH— group in compound 12 produced compounds 20 and 21, respectively, which were found to have less inhibitory activities with $IC_{50}$ values of 4.4 and 7.0 μM.

Replacing the two tert-butyl groups in compound 12 with less bulky isopropyl groups in compound 22 ($IC_{50}$=5.4 μM) led to ~8× activity reduction. Loss of activity for compound 23 with two n-butyl groups at these positions showed that longer alkyl substituents are disfavored. Changing to furan groups in compound 11 ($IC_{50}$=1.7 μM) also slightly reduced the inhibitory activity. In addition, compound 34 with a central furan core ($IC_{50}$=9.8 μM) was found to be considerably less active than the thiophene compound 12.

Example 1.4. Compound 2 is Competitive Against Histone

Figure 4A:
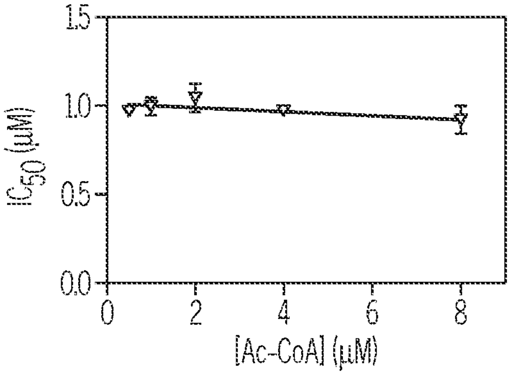
FIGS. 4A-4C illustrate that compound 12 is a competitive inhibitor of p300 HAT against the substrate histone.

Next, Applicant performed steady-state enzyme kinetics studies to investigate the mode of inhibition for the most potent inhibitor 12. Inhibitory activities of compound 12 were determined with varying concentrations of the cofactor Ac-CoA and the substrate histone. As shown in FIG. 4A, $IC_{50}$ values of 12 did not change with increasing concentrations of Ac-CoA (from 0.5-8 μM, or 0.07-1.2×$K_m$ (24)), indicating compound 12 is likely a non-competitive inhibitor against the enzyme cofactor. Its inhibitory activities were found to be reduced in a linear manner (FIG. 4A) when increasing concentrations of the substrate histone peptide (2-100 μM) were used in the assay, suggesting compound 12 is a competitive inhibitor against the substrate histone.

Figure 4B:
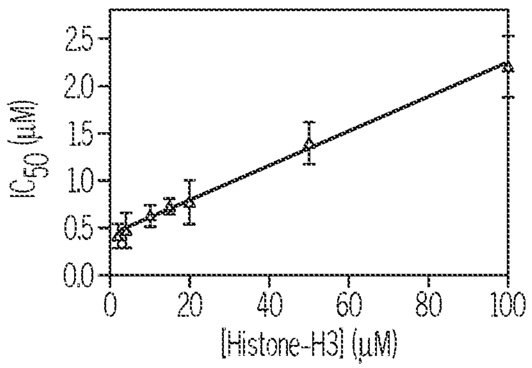

Next, Applicant used a reported Alpha (amplified luminescent proximity homogeneous assay) assay to confirm this finding. Upon excitation by a laser beam (680 nm), histone H4 coated donor beads generate singlet oxygen radicals, which can travel for a very short distance (<200 nm) in the solution and cannot reach the free acceptor beads. The binding between the histone peptide and p300 HAT brings the donor and acceptor beads together, which allows the radicals to activate the p300 HAT coated acceptor beads and produce luminescence at 570 nm (FIG. 4B). Use of histone H4 is because the assay with histone H3 did not produce a luminescence signal, presumably due to a weaker binding between p300 HAT and histone H3.

Figure 4C:
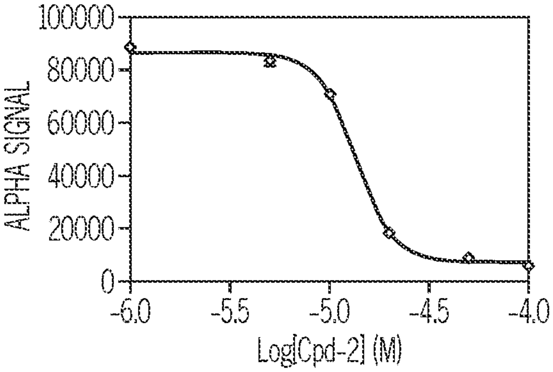

As shown in FIG. 4C, compound 12 can disrupt the binding between the protein and histone H4, and reduce the luminescence signal in a dose-dependent manner ($IC_{50}$=13.5 μM), showing the inhibitor is competitive against the substrate histone. This is in contrast to Ac-CoA competitive inhibitor A-485, which did not affect the binding between p300 HAT and histone H4(16). These results are of interest in that due to a different mode of inhibition, histone-competitive inhibitor 12 might have a different cellular activity or selectivity, as compared to Ac-CoA-competitive inhibitors A-485 and C646.

Example 1.5. Docking Studies

Next, Applicant performed molecular modeling to find possible binding structures of the most potent inhibitor 12 in p300 HAT. The program Glide in Schrödinger small-molecule drug discovery software suite was used for the docking studies, with the crystal structure of human p300 HAT in complex with Ac-CoA (PDB code 4PZS) (25) as a template.

Figure 5A:
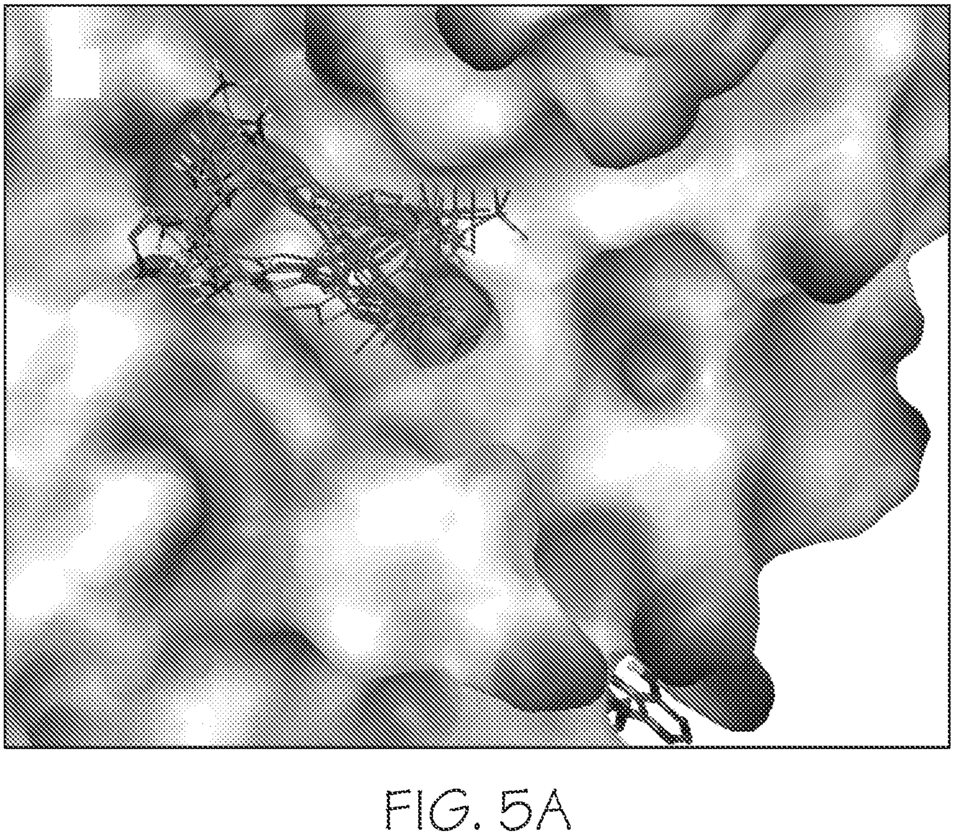
FIGS. 5A-5B show docking results for compound 12.
Figure 5B:
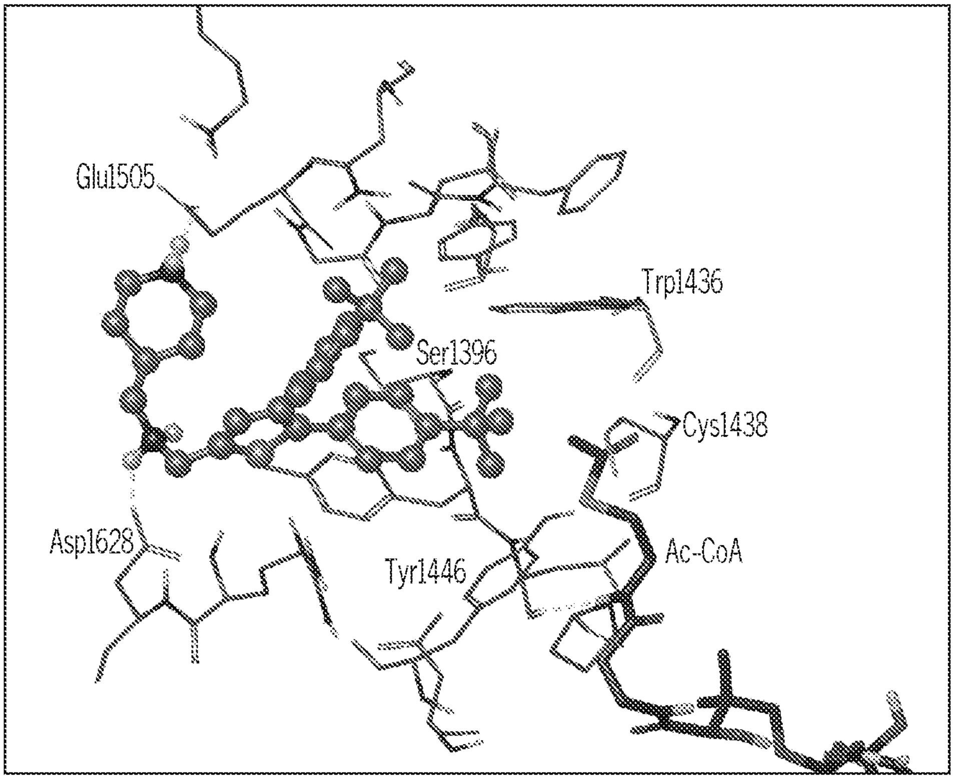

Since compound 12 is a competitive inhibitor against the substrate histone, Ac-CoA was treated as an integrate part of the protein. Upon protein structure preparation as well as docking grid generation, compound 12 was docked into the protein-Ac-CoA complex and the results are shown in FIGS. 5A and 5B. The inhibitor can be favorably docked into the protein, as the 10 distinct docking conformations of compound 12 with the lowest energies exhibit similar binding features (FIG. 5A).

One of the tert-butyl groups of these conformations is predicted to insert into and have favorable hydrophobic interactions with the so-called "lysine channel", through which the histone lysine sidechain inserts into p300 HAT, attacks the carbonyl of Ac-CoA, and gets acetylated. Residues Trp1436, Cys1438, Tyr1446 and Ser1396 form the lysine channel of p300 HAT (FIG. 5B).

As shown in FIG. 5B, the tert-butyl group is predicted to be ~3.5 Å from these residues with favorable van de Waals interactions. The central thiophene core and the two para-tert-butylphenyl groups of these structures have extensive hydrophobic interactions with either upper or lower surface of the protein (FIGS. 5A and 5B). In addition, the positively charged, two amino groups of many of these docking structures form hydrogen bonds and have favorable electrostatic interactions with Asp1628 and Glu1505, as exemplified in FIG. 5B. These favorable binding features are consistent with the strong inhibitory activity of compound 12.

Moreover, the docking results might be used to rationalize some of the observed SARs. For example, hydrogen bond/electrostatic interactions between the middle —NH— and Asp1628 are predicted to contribute significantly to the binding of compound 12. This could explain the loss of activity for compound 13 with an —O— linkage, which does not interact with the (negatively charged) Asp1628 sidechain. In addition, compound 1 is a good inhibitor, which might be due to favorable interactions between its —CONH— group and Asp1628.

Example 1.6. Enzyme Selectivity

Humans have three classes of histone/protein lysine acetyltransferases with distinct conserved motifs and structures, including p300/CBP, Gcn5-related N-acetyltransferase (GNAT) and MYST (MOZ, Ybf2, Sas2 and Tip60) family of HATs. Compound 12 was tested for its activities against selected HATs from these three classes of HATs. CBP is a homolog of p300. The HAT domains of CBP and p300 exhibit 87% identity in sequence. PCAF (p300/CBP associating factor) is a member of the GNAT family, while Myst3 belongs to the MYST family of HATs.

P300/CBP HATs have a distinct sequence and 3-dimensional structure from the GNAT and MYST HAT proteins.

As shown in Table 1, compound 12 was found to be also a strong inhibitor of human CBP HAT with an $IC_{50}$ of 1.2 μM, comparable to its $IC_{50}$ against p300 HAT. However, compound 12 did not significantly inhibit the activity of PCAF and Myst3 even at 20 μM, showing a high selectivity for p300/CBP HAT.

TABLE 1

| Inhibitory activities of compound 12 against HATs. | |
|---|---|
| | $IC_{50}$ (μM) |
| P300-HAT | 0.62 ± 0.12 |
| CBP-HAT | 1.2 ± 0.13 |
| PCAF | >20 (<10% inhibition at 20 μM) |
| Myst3 | >20 (<10% inhibition at 20 μM) |

Example 1.7. Inhibition of Cellular Histone Acetylation

Figure 6:
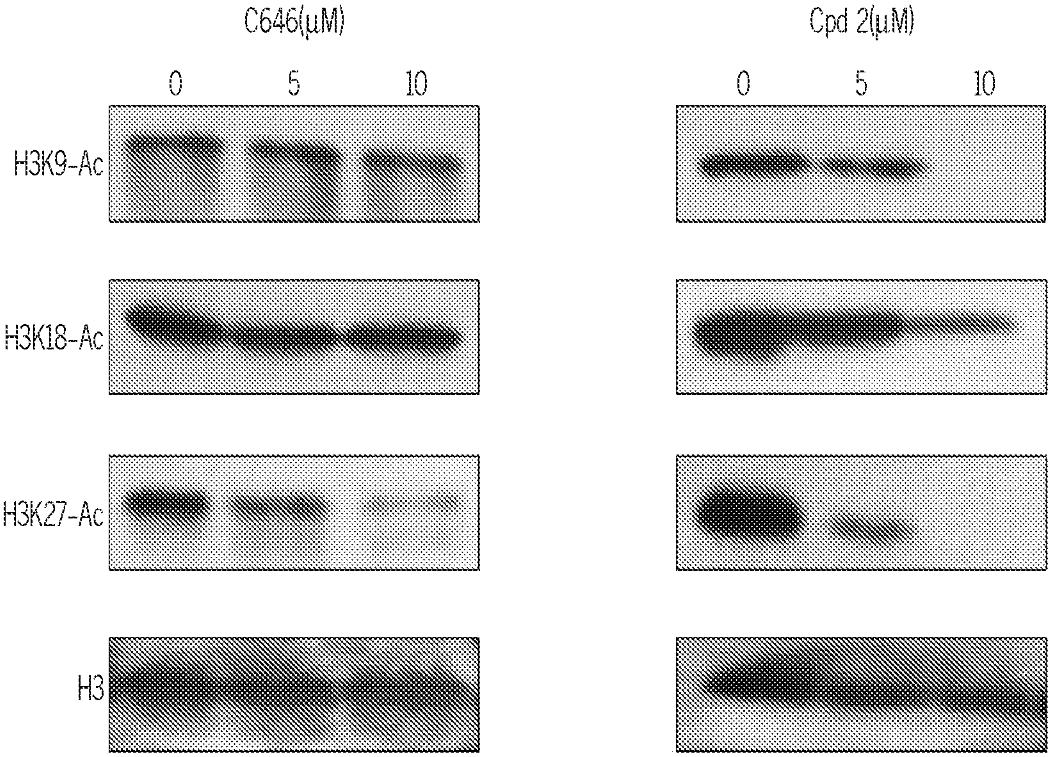
FIG. 6 provides results illustrating that compound 12 and C646 inhibited cellular acetylation of H3K9, H3K18 and H3K27.

Ability of compound 12 to inhibit cellular p300/CBP HAT was evaluated, together with a known inhibitor C646 as a comparison. Kasumi-1 leukemia cells were treated with increasing concentrations of these compounds for 12 h. Histone was extracted and subjected to electrophoresis separation and Western blot staining to determine levels of acetylation at various lysine residues. As shown in FIG. 6, compound 12 was found to significantly inhibit cellular acetylation of histone H3K9, H3K18 and H3K27 at 5 and 10 μM, in a dose dependent manner. H3K27 seems to be the most sensitive cellular substrate of p300 HAT. These results are consistent with previous studies of known inhibitors A-485 and C646. As compared to C646, compound 12 appeared to exhibit more potent cellular activities at these lysine residues. This might be due to different mode of inhibition or cell permeability for the two compounds.

Example 1.8. Inhibition of Tumor Cell Proliferation

Activity of compound 12 was tested against proliferation of several tumor cell lines in which p300/CBP HAT is of importance. First, ER-mediated transcription is critical to ER+breast cancer. It is an ordered, stepwise assembly of ER and coactivator proteins for gene expression. Upon binding with an estrogen molecule in cytoplasm, ER undergoes conformational changes, forms a homodimer, and is translocated into the nucleus, where ER binds to estrogen response element, a short segment of DNA within a gene promoter. Next, a steroid receptor coactivator (SRC) protein binds to ER, followed by recruitment of p300 through its SRC-binding SID domain.

P300 HAT activity is required for the ER-mediated gene expression, because a mutant p300 without the enzyme function failed to activate it. Given the critical role of p300-mediated histone acetylation in the ER signaling pathway, compound 12 was assessed for its activity against the $ER^+$ breast cancer cell line MCF-7. In addition, ER antagonist tamoxifen is widely used in the clinic to treat $ER^+$ breast cancer by suppressing ER mediated gene transcription. However, many patients eventually develop resistance to tamoxifen and die of the cancer.

Activity of compound 12 was also tested against tamoxifen-resistant MCF-7 to find whether inhibition of HAT can affect growth of these cells. As summarized in Table 2, compound 12 exhibited strong antiproliferative activity against parent MCF-7 cells ($EC_{50}$=2.8 μM) as well as tamoxifen-resistant cells ($EC_{50}$=3.4 μM). These results show that inhibition of p300-mediated histone acetylation can inhibit growth of MCF-7 breast cancer cells and such activity is independent upon the status of tamoxifen resistance, suggesting the p300 HAT inhibitor could have potential clinical applications in breast cancer therapy.

TABLE 2

| Antiproliferative activities of compound 12. | |
|---|---|
| | $EC_{50}$ (μM) |
| MCF-7 | 2.8 ± 0.1 |
| MCF-7 (Tam-R) | 3.4 ± 0.1 |
| PANC-1 | 1.0 ± 0.2 |
| MDA-PANC-28 | 2.8 ± 0.4 |
| Kasumi-1 | 2.6 ± 0.6 |

Moreover, p300 HAT activity has been reported to play important roles in pancreatic cancer and acute myeloid leukemia caused by oncogene RUNX1-ETO. Activity of compound 12 was evaluated against two pancreatic cancer cells PANC-1 and MDA-PANC-28 and RUNX1-ETO leukemia cell line Kasumi-1. As shown in Table 2, compound 12 showed potent activities against proliferation of the two pancreatic cancer cells with $EC_{50}$ values of 1.0 and 2.8 μM. It also inhibited growth of Kasumi-1 cells with an $EC_{50}$ of 2.6 μM.

Example 1.9. Gene Expression Profiling

RNA sequencing was used to investigate how treatment with p300 HAT inhibitor 12 affects gene expression in $ER^+$ breast cancer MCF-7 cells. Upon starvation (i.e., culturing in charcoal treated FBS without hydrophobic hormones including estrogens) for 7 days, MCF-7 cells were supplemented with estradiol (10 nM), followed by treatment with compound 12 for 2 days. Total RNA from three groups of MCF-7 cells, including starved, control (with estradiol) and treated (with estradiol and compound 12) groups, was purified, prepared and sequenced. RNA sequencing data were mapped onto the human genome and gene expression profiles were determined and normalized. Genes with significantly changed expression levels were determined using a two-sided parametric t-test with the p value of <0.05. Gene set enrichment analysis (GSEA)(31) was used to analyze significant gene expression changes between these three groups of MCF-7 cells.

First, to determine whether the observed cellular activities of compound 12 are due to inhibition of p300 HAT, we used GSEA to compare the transcriptional profile of the 12-treated MCF-7 cells with a publicly available p300 transcriptional signature (GSE31873), which was derived from siRNA-mediated p300 knockdown in C4-2B prostate cancer cells.

Figure 7A:
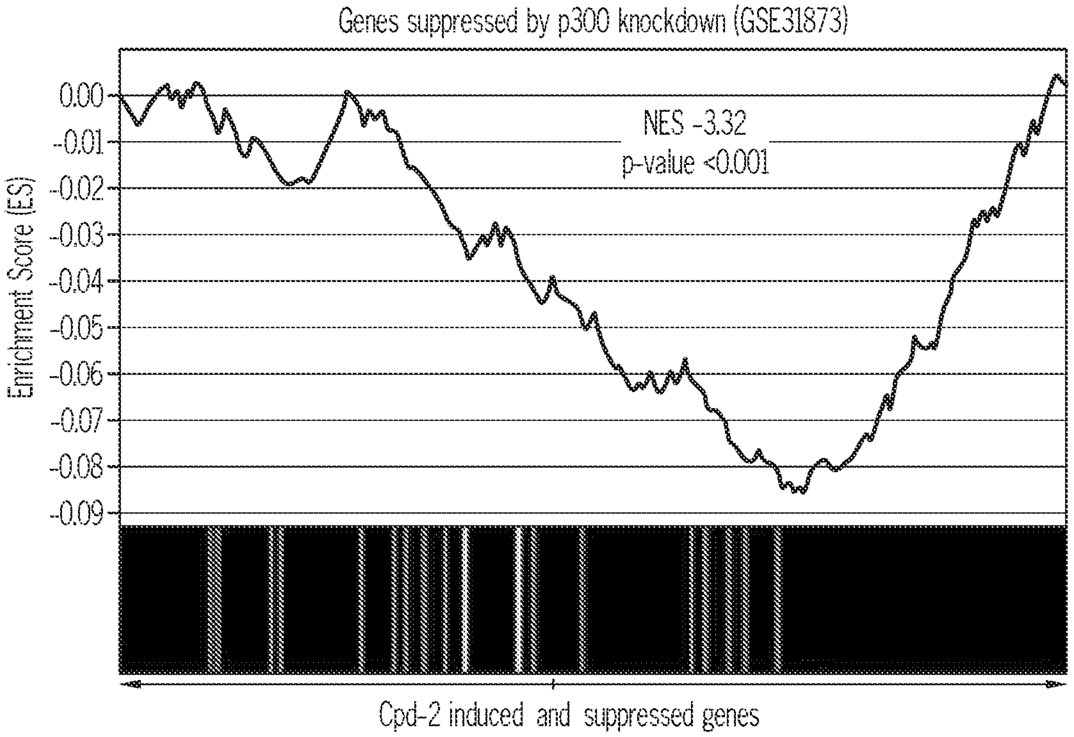

As shown in FIG. 7A, there is a strong concordance between the two transcriptional signatures: Genes suppressed by compound 12 were strongly enriched among those suppressed by p300 knockdown, with normalized enrichment score (NES) of −3.32 and p value of <0.001. This result demonstrates that treatment with the p300 HAT inhibitor mimics the transcriptional footprint of p300 depletion and supports that p300 HAT is the cellular target of compound 12.

Figure 7B:
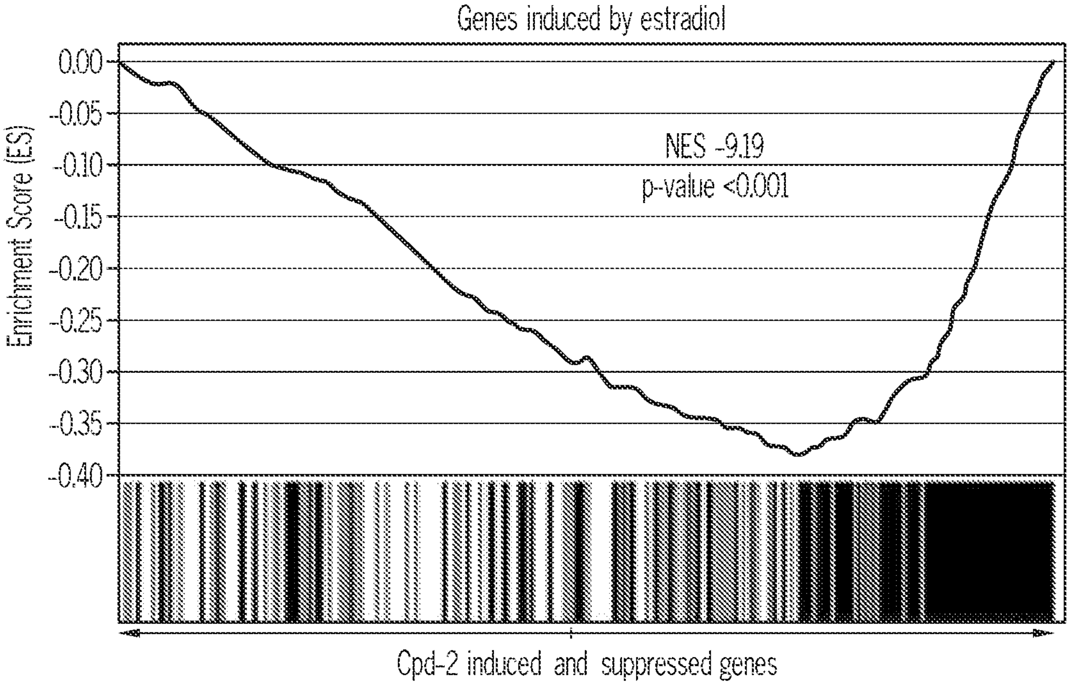
Figure 7C:
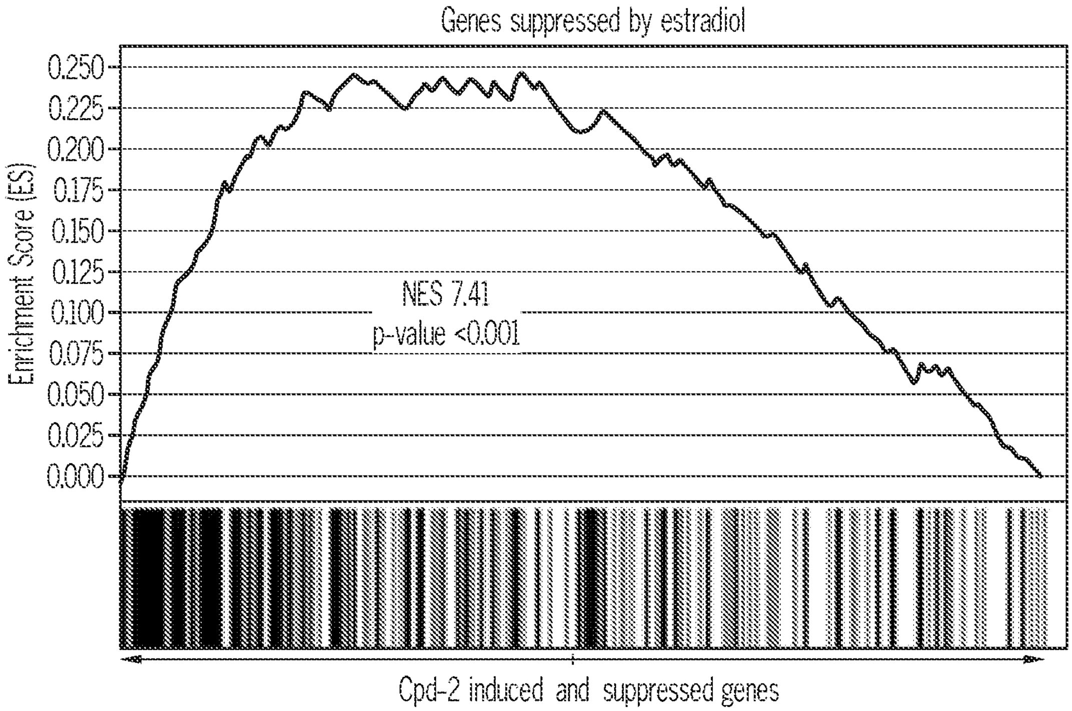

Next, activity of compound 12 in the ER signaling pathway was analyzed. As compared to starved cells, supplementation with estradiol potently caused upregulation as well as downregulation of several publicly available ER-related gene signatures in the control group of MCF-7 cells. Importantly, treatment with compound 12 counteracted such estrogen-induced gene transcription: The gene set upregulated by estradiol was strongly downregulated upon treatment with 12 (FIG. 7B, NES=−9.19 and p<0.001), and the genes suppressed by estradiol were significantly upregulated by compound 12 (FIG. 7C, NES=7.41 and p<0.001). These results are consistent with previous studies showing p300 HAT is essential for ER-mediated gene expression, and demonstrate that pharmacological inhibition of p300 HAT can offset the effects of estrogen in gene regulation.

Moreover, Applicant investigated gene expression changes caused by compound 12 in the context of cancer biology and therapy. As shown in FIG. 7D, global gene expression profiling analysis revealed that inhibition of p300 HAT by compound 12 counteracted estradiol and caused significant suppression of a number of estrogen-induced, cancer-related gene sets, including E2F and c-Myc gene signatures as well as those involved in cell proliferation, cell cycle, mitosis, DNA replication, DNA repair and self-renewal (stemness). Specifically for breast cancer, treatment with compound 12 downregulated a number of gene signatures that have previously been shown to be upregulated in multiple breast cancer patient datasets (as compared to normal breast tissues), associated with poor prognosis, cancer progression, invasion and relapse (FIG. 7E). Collectively, these GSEA results show the importance of p300 HAT in breast and other types of cancer, as well as the perspective for pharmacological inhibition of p300 HAT (by e.g., compound 12) in breast cancer therapy.

Example 1.10. Discussion

Histone acetylation by the HAT domain of p300/CBP has been found to play critical roles in many nuclear receptor-regulated signaling pathways, such as ER, AR and peroxisome proliferator-activated receptors (PPAR). Dysfunction of these gene transcription programs has been found in a number of diseases such as cancer and obesity. Moreover, p300/CBP has been found to directly contribute to oncogenesis (e.g., in RUNX1-ETO leukemia) or be part of a fusion oncogene due to chromosome translocation. Therefore, drug-like inhibitors of p300/CBP HAT are needed, which could be useful chemical probes and potential therapeutics for these indications. In addition, p300 and CBP are large proteins (~2,400 amino acids) with multiple other domains playing important physiological roles. They also share a high degree of homology with many duplicate functions. Given these two points, cell-permeable, small-molecule inhibitors of the HAT domain of p300/CBP are particularly useful for studying biological functions of p300/CBP HAT, because observed activities by genetic knockdown/knockout of p300 or CBP might not be relevant.

Compound screening followed by medicinal chemistry studies have led to the discovery of tri-substituted thiophene compound 12 that is a novel, small molecule inhibitor with an $IC_{50}$ of 620 nM against p300 HAT and 1.2 μM against CBP HAT. Compound 2 did not significantly inhibit two other major human HATs PCAF and Myst3 at 20 μM, showing a high selectivity. Biochemical studies showed that compound 12 is competitive against the substrate histone and non-competitive against the cofactor Ac-CoA, showing a distinct mode of inhibition from previous studied inhibitors C646 and A-485. Docking studies of 12 into the histone binding pocket of the p300 HAT structure provided possible binding models of the inhibitor in the protein.

In addition, compound 12 was found to be cell-permeable and inhibit cellular acetylation at several histone lysine residues, with H3K27 being the most sensitive substrate. With $EC_{50}$ of ~3 μM, compound 12 strongly inhibited proliferation of $ER^+$ breast cancer cell line MCF-7, regardless of its sensitivity or resistance to the commonly used estrogen antagonist tamoxifen, suggesting the potential therapeutic application of this compound in the context of endocrine resistance. Compound 12 also exhibited strong activity against growth of several pancreatic cancer cells and RUNX1-ETO leukemia cell Kasumi-1, in which p300 HAT is known to be important.

Global gene transcription profiling was performed to investigate the cellular target of compound 12 as well as the mechanism for its observed biological activities in MCF-7 cells. First, the overall transcriptional changes upon treatment with compound 12 recapitulated those caused by siRNA-mediated p300 knockdown. This result, together with its inhibitory activity in cellular histone lysine acetylation, support that p300 HAT is the cellular target of compound 12. Second, inhibition of p300 HAT activity by compound 12 significantly offset estrogen-induced gene expression, showing p300 HAT is essential for the ER activity. Moreover, treatment with compound 12 strongly downregulated a number of (general) cancer-related gene signatures, as well as gene sets that have been identified in the clinic for the progression, invasion, relapse and poor prognosis of breast cancer. These results, together with the compound's potent antiproliferative activities against several types of cancer cells, suggest that pharmacological inhibition of p300 HAT is a useful therapeutic approach to cancer treatment. In conclusion, Applicant's results demonstrate that compound 12 is not only a useful small-molecule probe for biological studies of p300/CBP HAT, but also a novel pharmacological lead for further drug development targeting breast and other types of cancer.

Example 1.11. Compound Synthesis and Characterization

Compound synthesis and characterization can be found in the Supplementary Information for the following reference: *J. Med. Chem.* 2020, 63, 9, 4716-4731. Compound synthesis and characterization can be found in priority U.S. Provisional Patent Application No. 63/007,711.

Example 1.12. Inhibition of p300-HAT and Other HATs

The HAT domain (1195-1673) of human p300 was cloned, inserted into pGEX-KG vector and the DNA sequence was verified by sequencing. The p300-HAT expression plasmid was transformed into *E. coli* BL21-CodonPlus strain (Agilent) and cultured at 37° C. in LB medium containing ampicillin (50 g/mL) and chloramphenicol (34 g/mL). After the optical density of the bacterial culture reached ~0.9 at 600 nm, p300 HAT expression was induced by adding 300 μM isopropylthiogalactoside (IPTG) at 18° C. for 48 hours. Cells were collected, lysed, centrifuged for 20 min at 20,000 rpm. The supernatant was subjected to column chromatography with glutathione sepharose resins. The recombinant GST-p300-HAT fusion protein was obtained in ~90% purity (SDS-PAGE) by elution with 10 mM of glutathione solution, which was further purified using a Superdex 200 gel filtration column chromatography. CBP, PCAF and Myst3 HATs were obtained using similar methods.

To determine inhibitory activity, a compound with concentrations ranging from 100 nM to 10 μM was incubated with p300-HAT (10 nM) in 20 μL of 50 mM phosphate buffer (pH=7.0) containing 0.01% Brij-35 for 10 min at 25° C. Histone H3 peptide (1-21) (20 μM) and Acetyl-CoA (1 μM $^{3}H$—Ac-CoA and 19 μM Ac-CoA) were added to initiate the reaction. After 30 min at 25° C., the reaction was stopped by adding 6 N formic acid (5 μL). 20 μL of reaction mixture was then transferred to a small piece of P81 filter paper (Whatman) that binds histone H3 peptide. The filter paper was washed 3× with 50 mM $NaHCO_3$, dried, and transferred into a scintillation vial containing 2 mL of scintillation cocktail. Radioactivity on the filter paper was measured with a Beckman LS-6500 scintillation counter. $IC_{50}$ values were obtained by using a standard sigmoidal dose response curve fitting in Prism (version 5.0, GraphPad Software, Inc., La Jolla, CA). $IC_{50}$ values were the mean values from at least three experiments.

Example 1.13. Alpha Assay

Applicant utilized an assay to investigate whether compound 12 can disrupt the binding of p300 HAT and histone H4 peptide. In brief, the assay was performed in a 384-well plate using His6-tagged P300 HAT (125 nM) coated nickel chelate acceptor beads (5 μL, Perkin Elmer), biotinylated H4 peptide [SGRGKGGKGLGKGGAKRHRKVLRGG-K (Biotin)-NH2](30 nM) coated streptavidin donor beads (5 μL, Perkin Elmer), and varying concentrations of 12 in a PBS buffer with 0.5% BSA (final volume of 25 μL). Upon incubation for 1 h, Alpha signal was determined (laser excitations at 680 nm and reading at 570 nm) using a Tecan Spark microplate reader. The $IC_{50}$ values were determined using the sigmoidal dose-response fitting in the program of Prism 5.0 (GraphPad).

Example 1.14. Molecular Modeling

Docking studies were performed with Schrödinger small-molecule drug discovery software suite (Schrödinger, LLC, New York, NY, 2017). The crystal structure of p300-HAT in complex with Ac-CoA (PDB: 4PZS) was prepared using the module "protein preparation wizard" in Maestro with the default protein parameters. Hydrogen atoms were added and water molecules were extracted. Ac-CoA was included in the protein structure for docking. Hydrogen bonds were optimized, the partial charges were assigned, and the protein structure was energy-minimized using OPLS-2005 force field. A receptor grid was generated using the program Glide without any constraints. Compound 11 was constructed, energy-minimized using OPLS-2005 force field in Maestro and then docked into the prepared protein structure using Glide (docking parameters: standard-precision and dock flexibly).

Example 1.15. Western Blot

About $10^6$ Kasumi-1 cells per well were incubated with compound 11 at 0, 5 and 10 μM for 12 hours. Histone proteins were extracted using EpiQuik total histone extraction kit (Epigentek), according to the manufacturer's protocol. Equal amounts of histones (2 μg) were separated on SDS-PAGE and transferred to PVDF membranes. The blots were probed with primary antibodies against H3K9Ac, H3K18Ac, H3K27Ac and H3 (Cell Signaling), followed by anti-rabbit IgG (Thermo Scientific) secondary antibodies.

Example 1.16. Cell Growth Inhibition

The anti-proliferation assays for non-breast cancer cells were done using a previously developed assay. In brief, for Kasumi-1 cells, $10^6$ cells per well were added into 96-well plates and cultured with increasing concentrations of a compound in RPMI-1640 medium supplemented with 20% fetal bovine serum and penicillin (100 U/mL) and streptomycin (100 g/mL) at 37° C. in a 5% C02 atmosphere with 100% humidity. For solid tumor cells, $10^5$ cells per well were added into 96-well plates and cultured in Dulbecco's Modified Eagle's Medium (DMEM) supplemented with 10% fetal bovine serum and penicillin (100 U/mL) and streptomycin (100 g/mL) overnight. Upon addition of increasing concentrations of a compound, cells were incubated for 5 days. Cell viability was assessed by using an XTT assay kit (Roche) for leukemia cells or an MTT assay (Sigma) for attachment cells. For the breast cancer MCF-7 cells, culture and inhibition assays were performed according to our previous methods in Ref. 25 and 26. Compound $EC_{50}$ values were calculated from dose response curves using Prism 5.0.

Example 1.17. RNA Extraction

Upon starvation (culturing in phenol red-free DMEM medium with 10% charcoal treated FBS to remove hydrophobic hormones such as estrogens) for 7 days, MCF-7 cells were treated with the p300 inhibitor (6 μM) or DMSO control, in the presence or absence of (10 nM) estradiol (E2) for 48 hours. Total RNA was extracted using RNeasy Plus Mini Kit (Qiagen), according to the manufacturer's instruction.

Example 1.18. Library Preparation

The RNA integrity for each sample was assessed with a RNA 6000 Nano chip on a 2100 Bioanalyzer (Agilent; Santa Clara, CA). The average RNA integrity score for the sample set was 6.48. Sequencing libraries were prepared using the TruSeq Stranded Total RNA Library Prep Kit (Illumina, Inc; San Diego, CA). Concisely, ribosomal RNA (rRNA) was depleted from total RNA where the remaining (ribo-depleted RNA) was purified, fragmented for 7.5 minutes, and primed for cDNA synthesis. Blunt-ended cDNA was generated after first and second strand synthesis. Adenylation of the 3' blunt-ends was followed by adapter ligation prior to the enrichment of the cDNA fragments. Final library quality control was carried out by measuring the fragment size on a DNA1000 chip on a 2100 BioAnalyzer (Agilent; Santa Clara, CA). The average library yielded an insert bp size of 258. The concentration of each library was determined by quantitative PCR (qPCR) by the KAPA Library Quantification Kit for Next Generation Sequencing (KAPA Biosystems; Woburn, MA).

Example 1.19. Sequencing

Libraries were normalized to 50 nmol/L in 10 mM Tris-Cl, pH8.5 with 0.1% Tween 20 then pooled evenly. The 50 nmol/L library pool was diluted to 2 nmol/L with 10 mM Tris-Cl, pH8.5 with 0.1% Tween 20. The pooled libraries were denatured with 0.05N NaOH and diluted to 20 pmol/L. Cluster generation of the denatured libraries was performed according to the manufacture's specifications (Illumina, Inc; San Diego, CA) utilizing the HiSeq Rapid PE Cluster Kit v2 chemistry and flow cell. Libraries were clustered appropriately with a 1% PhiX spike-in. Sequencing-by-synthesis (SBS) was performed on a HiSeq 2500 utilizing v2 chemistry with paired-end 101 bp reads and a 6 bp index read culminating in an average output of 20 million paired-end reads (or 40 million total reads) per sample. Sequence read data were processed and converted to FASTQ format by Illumina BaseSpace analysis software (v2.0.13).

Example 1.20. Bioinformatics Analysis

RNAseq data files were trimmed using Trim Galore!. Then the data was mapped using Hisat2 onto the human reference genome build UCSC hg38/GRCh38 and sorted using samtools. Gene expression was assessed and fragments per kilobase of transcript per million (FPKM) values were determined using Stringtie. Gene expression profiles were normalized using the quantile normalization method. Significantly changed genes were determined using a two-sided parametric t-test, with significance assessed at $p<0.05$, only genes for which at least one sample exceeded 1 FPKM in expression were considered. Enriched pathways were inferred using the Gene Set Enrichment (GSEA) method, and the Molecular Signature Database (MSigDB) pathway collection.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A composition comprising a compound, wherein the compound has the following structure:

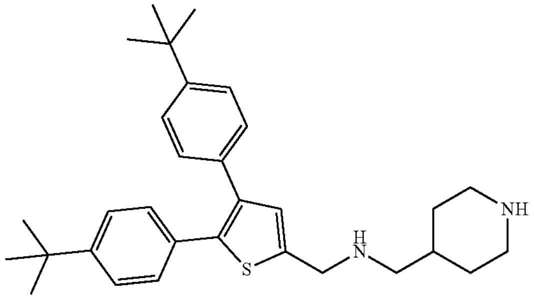 [SMILES: CC(C)(C)c1ccc(-c2cc(CNCC3CCNCC3)sc2-c2ccc(C(C)(C)C)cc2)cc1]

2. The composition of claim 1, wherein the composition further comprises a delivery agent.

3. The composition of claim 2, wherein the delivery agent is a nanoparticle.

4. The composition of claim 1, wherein the composition comprises at least one excipient agent selected from the group consisting of anti-adherents, binders, coatings, colors, disintegrants, flavors, glidants, lubricants, preservatives, sorbents, sweeteners, vehicles, or combinations thereof.

5. The composition of claim 1, wherein the composition comprises at least one solubilizing agent selected from the group consisting of polyethylene glycol, glycerin, propylene glycol, ethanol, sorbitol, polyoxyethylated glycerides, polyoxyethylated oleic glycerides, polysorbates, sorbitan monooleate, hydroxypropyl-beta-cyclodextrin (HPCD), polyoxyl 40 hydrogenated castor oil, polyoxyl hydroxystearates, or combinations thereof.

* * * * *